(12) United States Patent
Madara et al.

(10) Patent No.: US 8,440,718 B2
(45) Date of Patent: *May 14, 2013

(54) MODULATION OF INFLAMMATION RELATED TO COLUMNAR EPITHELIA

(75) Inventors: James L. Madara, Winchester, MA (US); Charles N. Serhan, Needham, MA (US); Sean P. Colgan, Newton, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/762,388

(22) Filed: Jan. 22, 2004

(65) Prior Publication Data

US 2004/0151712 A1 Aug. 5, 2004

Related U.S. Application Data

(60) Continuation of application No. 10/253,316, filed on Sep. 24, 2002, now Pat. No. 6,699,905, which is a continuation of application No. 09/972,419, filed on Oct. 5, 2001, now Pat. No. 6,458,839, which is a continuation of application No. 08/955,860, filed on Oct. 21, 1997, now Pat. No. 6,329,425, which is a division of application No. 08/806,278, filed on Feb. 25, 1997, now Pat. No. 6,100,296, which is a division of application No. 09/268,249, filed on Jun. 29, 2004, now Pat. No. 5,650,425, which is a continuation-in-part of application No. 08/084,311, filed on Jun. 29, 2003, now abandoned, which is a continuation-in-part of application No. 07/748,349, filed on Aug. 22, 1991, now abandoned, which is a continuation-in-part of application No. 07/677,388, filed on Apr. 1, 1991.

(51) Int. Cl.
*A61K 31/23* (2006.01)

(52) U.S. Cl.
USPC .......................................... 514/552; 514/559

(58) Field of Classification Search .................. 514/530, 514/552, 559, 573
See application file for complete search history.

(56) References Cited

U.S. PATENT DOCUMENTS

| | | | |
|---|---|---|---|
| 5,441,951 | A | 8/1995 | Serhan |
| 5,648,512 | A | 7/1997 | Serhan |
| 6,353,026 | B1 | 3/2002 | Serhan |
| 6,458,839 | B1 | 10/2002 | Madara et al. |
| 6,699,905 | B2 | 3/2004 | Madara et al. |

FOREIGN PATENT DOCUMENTS

| | | |
|---|---|---|
| JP | 63-17825 | 1/1988 |
| WO | WO 90/13292 | * 11/1990 |
| WO | WO 94/29262 | 12/1994 |
| WO | WO 95/01179 | 1/1995 |
| WO | WO 00/54767 | 9/2000 |

OTHER PUBLICATIONS

Weissmann, G., Smolen, J. E., and Korchak, H. M. (1980) Release of inflammatory mediators from stimulated neutrophils. *N. EngL J. Med.* 303, 27-34.
Serhan, C. N., Haeggstrom, J. Z., and Leslie, C. C. (1996) Lipid mediator networks in cell signaling: update and impact of cytokines. *FASEB J.* 10, 1147-1158.
Weiss, S. J. (1989) Tissue destruction by neutrophils. *N. Engl. J. Med.* 320, 365-376.
Serhan, C. N. (1994) Lipoxin biosynthesis and its impact in inflammatory and vascular events. *Biochim. Biophys. Acta* 1212, 1-25.
Borgeat, P., and Naccache, P. H. (1990) Biosynthesis and biological activity of leukotriene $B_4$. *Clin. Biochem.* 23, 459-468.
Yokomizo, T., Izumi, T., Chang, K., Takuwa, T., and Shimizu, T. (1997) A G-protein-coupled receptor for leukotriene $B_4$ that mediates chemotaxis. *Nature* 387, 620-624.
Fiore, S., Romano, M., Reardon, E. M., and Serhan, C. N. (1993) Induction of functional lipoxin $A_4$ receptors in HL-60 cells. *Blood* 81, 3395-3403.
Isakson, P., Seibert, K., Masferrer, J., Salvemini, D., Lee, L., and Needleman, P. (1995) Discovery of a better aspirin. *Advances in Prostaglandin, Thromboxane & Leukotriene Research* 23, 49-54.
Chiang, N., Takano, T., Clish, C. B., Petasis, N. A., Tai, H.-H., and Serhan, C. N. (1998) Aspirin-triggered 15-epi-lipoxin $A_4$ (ATL) generation by human leukocytes and murine peritonitis exudates: development of a specific 15-epi-$LXA_4$ ELISA. *J. Pharmacol Exper. Ther.* 287, 779-790.
Serhan, C. N., Maddox, J. F., Petasis, N. A., Akritopoulou-Zanze, I., Papayianni, A., Brady, H. R., Colgan, S. P., and Madara, J. L. (1995) Design of lipoxin $A_4$ stable analogs that block transmigration and adhesion of human neutrophils. *Biochemistry* 34, 1 4609-1 461 5.
Takano, T., Fiore, S., Maddox, J. F., Brady,:H. R., Petasis, N. A., and Serhan, C. N. (1997) Aspirin-triggered 15-epi-lipoxin $A_4$ ($LXA_4$) and $LXA_4$ Stable analogues are potent inhibitors of acute inflammation: Evidence for anti-inflammatory receptors. *J. Exp. Med.* 185, 1693-1704.
Owman, C., Garzino-Demo, A., Cocchi, F., Popovic, M., Sabirsh, A., and Gallo, R. (1998) The leukotriene $B_4$ receptor functions as a novel type of coreceptor mediating entry of primary HIV-1 isolates into CD4-positive cells. *Proc. Natl. Acad. Sci.* 95, 9530-9534.
Marcus, A. J. (1995) Aspirin as prophylaxis against colorectal cancer. *N. Engl. J. Med.* 333, 656-658.
Vainio, H., and Morgan, G. (1997) Aspirin for the second hundred years: new uses for an old drug. *Pharmacol Toxicol* 81, 151-152.
Herschman, H. R. (1998) Recent progress in the cellular and molecular biology of prostaglandin synthesis. *Trends in Cardiovasc. Med.* 8, 145-150.
Takano, T., Clish, C. B., Gronert, K., Petasis, N., and Serhan, C. N. (1998) Neutrophil-mediated changes in vascular permeability are inhibited by topical application of aspirin-triggered 15-epi-lipoxin $A_4$ and novel lipoxin $B_4$ stable analogues. *J. Clin. Invest.* 101, 819-826.

(Continued)

*Primary Examiner* — Zohreh Fay
(74) *Attorney, Agent, or Firm* — Scott D. Rothenberger; Fulbright & Jaworski L.L.P.

(57) ABSTRACT

This invention provides pharmaceutical compositions containing lipoxin compounds and therapeutic uses for the compounds in treating or preventing a disease or condition associated with columnar epithelial inflammation. The invention also discloses methods for screening for compounds useful in preventing columnar epithelial inflammation.

1 Claim, No Drawings

OTHER PUBLICATIONS

Billah, M. M., Eckel, S., Mullmann, T. J., Egan, R. W., and Siegel, M. I. (1989) Phosphatidylcholine hydrolysis by phospholipase D determines phosphatidate and diglyceride levels in chemotactic peptide-stimulated human neutrophils. Involvement of phsophatidate phosphohydrolase in signal transduction. *J. Biol. Chem.* 264, 17069-17077.

Wakelam, M. J. O., Martin, A., Hodgkin, M. N.; Brown, F., Pettit, T. R., Cross, M. J., De Takats, P. G., and Reynolds, J. L. (1997) Role and regulation of phospholipase D activity in normal and cancer cells. *Advances in Enzyme Regulation* 37, 29-34.

Olson, S. C., and Lambeth, J. D. (1996) Biochemistry and cell biology of phospholipase D in human neutrophils. *Chem. Phys. Lipids* 80, 3-19.

Steed, P. M., Clark, K. L., Boyar, W. C., and Lasala, D. J. (1998) Characterization of human PLD2 and the analysis of PLD isoform splice variants. *FASEB J.* 12, 1309-1317.

Martin, A., Saqib, K. M., Hodgkin, M. N., Brown, F. D., Pettit, T. R., Armstrong, S., and Wakelam, M. J. O. (1997) Role and regulation or phospholipase D signalling. *Biochem. Soc. Trans.* 25, 1157-1160.

Levy, B. D., Petasis, N. A., and Serhan, C. N. (1997) Polyisoprenyl phosphates in intracellular signalling. *Nature* 389, 985-989.

Agwu, D. E., McPhail, L. C., Sozzani, S., Bass, D. A., and McCall, C. E. (1991) Phosphatidic acid as a second messenger in human polymorphonuclear leukocytes. Effects on activation of NADPH oxidase. *J. Clin. Invest.* 88, 531-539.

Pettit, T. R., Martin, A., Horton, T., Liossis, C., Lord, J. M., and Wakelam, M. J. O. (1997) Diacylglycerol and phosphatidate generated by phospholipases C and D, respectively, have distinct fatty acid compositions and functions. *J. Biol. Chem.* 272, 17354-17359.

Gomez-Cambronero, J. (1995) Immunoprecipitation of a phospholipase D activity with antiphosphotyrosine antibodies. *J. Interferon Cytokine Res.* 15, 877-885.

Abousalham, A., Riviere, M., Teissere, M., and Verger, R. (1993) Improved purification and biochemical characterization of phospholipase D from, cabbage. *Biochim. Biophys. Acta* 1158, 1-7.

Zhou, H.-L., Chabot-Fletcher, M., Foley, J. J., Sarau, H. M., Tzimas, M. N., Winkler, J. D., and Torphy, T. J. (1993) Association between leukotriene $B_4$-induced phospholipase D activation and degranulation of human neutrophils. *Biochem. Pharmacol.* 46, 139-148.

Shechter, I., Fogelman, A. M., and Popjak, G. (1980) A deficiency of mixed function oxidase activities in the cholesterol biosynthetic pathway of human granulocytes. *J. Lipid Res.* 21, 277-283.

Rabinowitz, J. L., Baker, D. G., Villanueva, T. G., Asanza, A. P., and Capuzzi, D. M. (1992) Liver lipid profiles of adults taking therapeutic doses of aspirin. *Lipids* 27, 311-314.

Claria, J., and Serhan, C. N. (1995) Aspirin triggers previously undescribed bioactive eicosanoids by human endothelial cell-leukocyte interactions. *Proc. Natl. Acad. Sci.* 92, 9475-9479.

Serhan, C. N. (1997) Lipoxins and Novel Aspirin-Triggered 15-epi-Lipoxins: A Jungle of Cell-Cell Interactions or a Therapeutic Opportunity? *Prostaglandins* 53, 107-137.

Exton, J. H. (1997) New developments in phoipholipase D. *J. Biol. Chem.* 272, 15579-15582.

Fensome, A., Whatmore, J., Morgan, C., Jones, D., and Cockcroft, S. (1998) ADP-ribosylation factor and Rho proteins mediate fMLP-dependent activation of phospholipase D in human neutrophils. *J. Biol. Chem.* 273, 13157-13164.

Jarstfer, M. B., Blagg, B. S. J., Rogers, D. H., and Poulter, C. D. (1996) Biosynthesis of squalene. Evidence for a tertiary cyclopropylcarbinyl cationic intermediate in the rearrangement of presqualene diphosphate to squalene. *J. Chem. Soc.* 118, 13089-13090.

Bach, T. J. (1995) Some new aspects of isoprenoid biosynthesis in plants—a review. *Lipids* 30, 191-202.

Serhan et al., "Aspirin-Triggered 15-EPI-Lipoxin $A_4$ and Novel Lipoxin $B_4$ Stable Analogs Inhibit Neutrophil-Mediated Changes in Vascular Permeability," *Advances in Experimental Medicine and Biology*, vol. 469, 1999, pp. 287-293.

Gewirtz et al., "Pathogen-Induced Chemokine Secretion from Model Intestinal Epithelium is Inhibited by Lipoxin $A_4$ Analogs", *Journal of Clinical Investigation*, vol. 101, No. 9, May 1998, pp. 1860-1869.

Hansson et al., "Activation of Protein Kinase C by Lipoxin A and Other Eicosandoids. Intracellular Action of Oxygenation Products of Arachidonic Acid", *Biochemical and Biophysical Research Communications*, vol. 134, No. 3, 1986, pp. 1215-1222.

Olson et al., "Biochemistry and cell biology of phospholipase D in human neutrophils", Chemistry and Physics of Lipids, 80, pp. 3-19, 1996.

Takano et al., "Neutrophil-mediated Changes in Vascular Permeability Are Inhibited by Topical Application of Aspirin-triggered 15-epi-lipoxin $A_4$ and Novel Lipoxin $B_4$ Stable Analogues", J. Clin. Invest. vol. 101, No. 4, Feb. 1998, pp. 819-826.

\* cited by examiner

MODULATION OF INFLAMMATION RELATED TO COLUMNAR EPITHELIA

RELATED APPLICATIONS

This application is a continuation of U.S. Ser. No. 10/253,316, filed Sep. 24, 2002, now U.S. Pat. No. 6,699,905, issued Mar. 2, 2004, which is a continuation of U.S. Ser. No. 09/972,419, filed Oct. 5, 2001, now U.S. Pat. No. 6,458,839, issued Oct. 1, 2002, which is a continuation of U.S. Ser. No. 08/955,860, filed Oct. 21, 1997, now U.S. Pat. No. 6,329,425, issued Dec. 11, 2001, which is a divisional of U.S. Ser. No. 08/806,278, filed Feb. 25, 1997, now U.S. Pat. No. 6,100,296, issued Aug. 8, 2000, which is a divisional of U.S. Ser. No. 08/268,049 filed Jun. 29, 1994, now U.S. Pat. No. 5,650,435, issued Jul. 22, 1997,which is a continuation-in-part application of U.S. Ser. No. 08/084,311 filed Jun. 29, 1993, now abandoned, which is a continuation-in-part application of U.S. Ser. No. 07/748,349, filed Aug. 22, 1991, now abandoned, which is a continuation-in-part application of U.S. Ser. No. 07/677,388, filed Apr. 1, 1991, now abandoned. The contents of the aforementioned applications are hereby incorporated by reference in their entirety.

GOVERNMENT SUPPORT

The work leading to this invention was supported by at least one grant from the U.S. Government. The U.S. Government, therefore, may be entitled to certain rights in the invention.

BACKGROUND

Columnar epithelia exist in the lungs, kidneys, bladder, bile ducts, pancreatic ducts, gall bladder, testicles, thyroid, trachea, intestine, stomach, and liver. In many disease states, polymorphonuclear leukocytes (PMN) migrate across these epithelia. (Yardley J. H., et al. (1977). *In The Gastrointestinal Tract*. Yardley and B. C. Morson, editors. Williams and Wilkins Co., Baltimore. 57.) (Yardley, J. H. (1986). *In Recent Developments in the Therapy of Inflammatory Bowel Disease. Proceedings of a Symposium*. Myerhoff Center for Digestive Disease at Johns Hopkins, Baltimore. 3-9.) This migration of PMN is an early event in the mechanism of epithelial perturbation, which includes one or more of the following events: abnormal fluid and electrolyte transport, specific epithelial barrier dysfunction, and ultimately mucosal breakdown. These perturbations lead to chronic and episodic inflammatory conditions.

Epithelial perturbations cause or contribute to many inflammatory disease states including: gastritis, diverticulitis, cystic fibrosis, infectious colitis, bronchitis, asthma, Crohn's disease, nephritis, alveolitis, intestinal ulcers, idiopathic AIDS enteropathy, gastroenteritis, ischemic diseases, and glomerulonephritis. The efficacy of existing therapy for epithelial inflammation, such as methotrexate or corticosteroids, is highly unsatisfactory, partially due to a high toxicity which produces severe, adverse effects such as bone-weakening and systemic immunosuppression. (Physician's Desk Reference (41 st ed., 1987) Medical Economics Co., Inc. 1103-1104.) Even under ideal bioavailability conditions, the existing treatments fail to mechanistically target columnar epithelial inflammation.

New treatments for epithelial inflammation are needed.

SUMMARY OF INVENTION

This instant invention discloses new methods and compositions for treating or preventing inflammation which is caused or contributed to by the perturbation of columnar epithelia in a subject. The new pharmaceutical compositions comprise natural lipoxin $A_4$ or analogs of lipoxin $A_4$. And the new methods comprise administering to a subject having a columnar epithelial inflammatory disease an effective, anti-inflammatory amount of natural lipoxin $A_4$ or a lipoxin $A_4$ analog.

Natural lipoxin $A_4$ and analogs are thought to effect their anti-inhibitory activity by interfering with the interaction between polymorphonuclear (PMN) cells and columnar epithelium. Migration of PMN is an early event in the mechanism of epithelial perturbation which leads to mucosal breakdown, epithelial dysfunction, and chronic inflammatory conditions. As disclosed herein, prior exposure of polymorphonuclear leukocytes (PMN) to certain lipoxin compounds alters subsequent PMN migration across the columnar epithelium, thereby preventing an inflammatory response. By inhibiting an early event in the mechanism; $LXA_4$ effectively targets inflammation and inflammatory responses caused or contributed to by epithelial perturbation.

$LXA_4$, is a naturally-occuring tetraene-containing eicosanoids. Therefore, pharmaceutical compositions of $LXA_4$ or analogs thereof would expected to be biocompatible. In addition, because $LXA_4$ and analogs thereof are highly potent in vivo, relatively small doses can be administered to produce a therapeutic effect. In addition, natural lipoxins are subject to metabolic transformations in situ, that would further minimize any toxic, adverse effects, or adverse drug interactions. Alternatively, the instant invention discloses $LXA_4$ analogs that are relatively resistant to in vivo degradation and therefore, if shown to be safe, can be administered for a more prolonged therapeutic effect Lipophilic $LXA_4$ can be actively absorbed by columnar epithelial tissue.

For the reasons stated above, pharmaceutical compositions of natural $LXA_4$ or analogs thereof provide a superior drug for treating columnar epithelial inflammatory diseases. Additional features and advantages of the invention will become more apparent from the following detailed description and claims.

DETAILED DESCRIPTION OF THE INVENTION

This invention pertains to methods for treating or preventing inflammation or an inflammatory response caused or contributed to by the perturbation of a columnar epithelium. The term "columnar epithelium" is intended to mean one or more of the epithelia of the intestine, kidney, stomach, liver, thyroid, trachea, lung, gall bladder, urinary bladder, bile ducts, pancreatic ducts, liver, and testicles. A columnar epithelium performs three functions. First, it acts as a physical barrier. Second, it moves fluids, electrolytes, and nutrients in vectors across the epithelium. Third, it synthesizes and releases bioactive molecules to influence other cell types.

An epithelial perturbation is a deleterious alteration of one or more of the following: the normal barrier function; the transportation of fluids, electrolytes, or nutrients; or the synthesis or release of bioactive molecules by the epithelial cells. The term "epithelial perturbation" is meant to include one or more of the following events: abnormal fluid and electrolyte transport, especially chloride ion secretion, specific epithelial barrier dysfunction, and eventual mucosal breakdown. These perturbations lead to chronic and episodic inflammatory conditions.

This invention provides, in part, a method of screening for a compound which attenuates abnormal fluid and electrolyte trnsportation, which may or may not be caused by activated inflammatory cells. This invention also provides a method of treating or preventing the symptoms of abnormal fluid and electrolyte transportation, such as secretory diarrhea by administering to a subject of an effective amount of a natural lipoxin or lipoxin analog, or combination thereof, to reduce or prevent an epithelial perturbation of fluid and electrolyte transportation.

Activation of one or more types of inflammatory cells can mediate this inflammatory perturbation by inducing inflammatory cell action in the form of adhesion, migration, the release of bioactive molecules, or a combination thereof. Nonlimiting examples of inflammatory cells are leukocytes, which encompass polymorphonuclear leukocytes (PMN), eosinophils, T-lymphocytes, B-lymphocytes, natural killer cells, and monocyte/macrophages. For example, migration of PMN across the epithelium of the intestine is an early event in the perturbation mechanism. The term "migration" is meant to include both the adhesion of PMN to the epithelium and the complete traversion across the epithelium to the other side. Under normal circumstances, PMN rarely adhere to the epithelial surface, and thus such adhesion is considered the rate-limiting step in the migratory process.

This invention provides, in part, a method of screening for a compound which inhibits the activation of inflammatory cells, such as PMN, which interact with an epithelium. This method evaluates the anti-inflammatory action of an eicosanoid, such as a lipoxin, a lipoxin analog, or a combination thereof, based on the extent of its inhibition of PMN migration in the basal-to-apical direction. This invention also provides a method of treating or preventing inflammation or the inflammatory response caused or contributed to by activation of inflammatory cells. This method is the administration to a subject of an effective amount of a lipoxin or lipoxin analog, or combination thereof, to reduce or prevent inflammatory cell activation and the consequent inflammatory response.

This invention is based, in part, upon the finding that prior exposure of PMN to nanomolar concentrations of lipoxin $A_4$ ($LXA_4$) and certain lipoxin analogs modify subsequent PMN migration across an epithelial barrier. The effect was found to be dependent on the direction of PMN transepithelial migration: $LXA_4$ inhibited the number of migrating PMN cells in the basal-to-apical direction, but promoted the number of migrating PMN cells in the apical-to-basal direction. In a typical embodiment of the screening method, the basal-to-apical inhibition represented a decrease of 25%, and the apical-to-basal promotion represented an increase of 80%, after pretreatment of PMN with $LXA_4$ (10 nM) for 15 minutes.

Inflammatory Diseases of Columnar Epithelia

Epithelial perturbations cause or contribute to inflammatory intestinal disease states including: acute self-limited enterocolitis; viral infections such as non-specific enteritis or specific viral enteritis; ulcerative colitis; Crohn's disease; diverticulitis; bacterial enterocolitis, such as salmonellosis, shigellosis, campylobacter enterocolitis, or yersinia enterocolitis; protozoan infections such as amebiasis; helminthic infection; and pseudomembraneous colitis.

Additional inflammatory intestinal diseases are duodenitis resulting caused by infections, physical and chemical injuries, Celiac disease, allergic disease, immune disorders or stress ulcers; lymphocytic colitis; collagenous colitis; diversion-related colitis; acute self-limited colitis; microscopic colitis; solitary rectal ulcer syndrome; Behcet's disease; nonspecific ulcers of the colon; secondary ulcers of the colon; ischemic bowel disease; vasculitis; peptic duodenitis; peptic ulcer; bypass enteritis; ulcerative jejunoileitis; or nonspecific ulcers of the small intestine. Malabsorptive disorders include mucosal lesions associated with altered immune response such as idiopathic AIDS enteropathy, with viral or bacterial infections, or with miscellaneous diseases such as mastocytosis or eosinophilic gastroenteritis.

Perturbations of the epithelia of the lung and trachea cause or contribute to inflammatory lung diseases such as: cystic fibrosis, bronchiolitis, bronchitis, asthma, interstitial lung disease, eosinophilic pneumonias, tracheobronchitis, tracheoesophageal fistulas, and alveolitis.

Perturbations of the epithelium of the kidney cause or contribute to diseases such as: glomerulonephritis, nephritis, polycystic disease, ischemic disease, imrnune-complex-induced disease, immunopathogenic injuries, pyelonephritis, and tubulointerstitial disease.

Perturbations of the epithelium of the stomach cause or contribute to diseases such as gastritis and stomach ulcers.

This invention also encompasses inflammation of columnar epithelial caused or contributed to by surgery, allergy, chemical exposure, and physical injury.

Methods of Screening for Anti-inflammatory Compounds

This invention provides a method of screening for a compound which inhibits activation of inflammatory cells which interact with an epithelium. This method comprises pretreating the inflammatory cell with the compound, placing the pretreated cell on one side of a prepared epithelial barrier having a chemotactic agent on the other side, and determining whether the compound inhibits the activation of the inflammatory cell. Nonlimiting examples of inflammatory cells are leukocytes such as polymorphonuclear leukocytes (PMN), eosinophils, T-lymphocytes, B-lymphocytes, natural killer cells, and monocyte-macrophages. Inflammatory cell activation includes adhesion to the epithelium migration across the epithelium, release of bioactive molecules, or a combination thereof.

The epithelial barrier can be constructed by growing epithelial cells and forming a monolayer by controlling the growth media to preserve the polarized phenotype. For example, T84 cells are grown as monolayers in a 1:1 mixture of Dulbecco-Vogt modified Eagle's medium and Ham's F12 medium supplemented with 15 mM $Na^+$-HEPES buffer, pH 7.5, 1.2 g/l $NaHCO_3$, 40 mg/l penicillin, 8 mg/l ampicillin, 90 mg/l streptomycin, and 5% newborn bovine serum.

Normal or inverted monolayers can be constructed using the commercially available insert system (Costar inserts, 0.33 $cm^2$, 5 μm polycarbonate fibers, Cambridge, Mass.). The larger pore size is crucial to allow inflammatory cells to penetrate the filter. Furthermore, the filter must be coated with Collagen I to allow epithelial cell attachment. Prepared monolayers should be used within 6-14 days, since not only do physiologic responses diminish with time, but also cell processes can eventually move through the 51 μm pores and result in a doubled monolayer, with one monolayer on each side of the filter. The monolayer may be inverted or not, to allow screening for migration, adhesion, or release of bioactive molecules in both the apical-to-basal direction and the basal-to-apical direction.

Nonlimiting examples of cells from which to form the epithelial barrier include: the intestinal cell lines Caco-2 (ATCC accession number HTB 37), IEC-6 (ATCC accession number CRL 1592), T84 (ATCC accession number CCL 248) or HT-29 (ATCC accession number HTB 38); the renal tubular cell lines MDCK (ATCC accession numbers CCL 34 and CRL 6253) or LLC-$PK_1$ (ATCC accession numbers CL 101 and CRL 1392); and isolated alveolar epithelial cells grown in primary culture.

The prepared epithelial barrier may optionally have a permeable artificial membrane on one side to prevent membrane-membrane contact between the epithelial barrier and the inflammatory cell. While there are numerous artifical supports available, a preferable membrane made of polycarbonate may be obtained commercially from Costar Corp., Cambridge, Mass.

The epithelial barrier also may have cell-sized objects (approximately 7-10 μm in diameter) located in the interstitial spaces between the epithelial barrier cells. These objects can be actual cells, or latex beads. The latex beads can be inert or coated with one or more types of active molecules attached to the bead surface, such as marker molecules, signal molecules, or monoclonal antibodies. The inert beads are available commercially (Seradyne, Indianapolis, Ind.). The beads mimic the physical presence of inflammatory cells. In addition, the coated beads provide a high local concentration of the coating molecule(s) and mimic the structural stability of cell-cell membrane contact. Furthermore, the beads provide a method of introducing bioactive molecules of otherwise low solubility into the system for long periods of time. The beads may be coated with a particular selected molecule, without undue experimentation, by methods known to those skilled in the art.

A chemotactic agent elicits the adhesion, migration, release of a bioactive molecule, or combination thereof by the inflammatory cells on the opposite side of the epithelial barrier. Nonlimiting examples of an appropriate chemotactic agent are: eicosanoids such as leukotriene $B_4$(LTB4), 12-hydroxy-5,8,11-cis-13-trans-eicosatetraenoic acid (12-HETE), and 5S-hydroxy-8,11,14 cis-6-trans-eicosatetraenoic acid (5-HETE); IL-8, IGF-β, C5a, platelet activating factor (PAF), and N-formyl-Met-Leu-Phe (fMLP). In addition, any microbial pathogen-derived chemotactic factor may be used, since fMLP is a model attractant for bacterial chemotaxis. The amount of chemoattractant should be sufficient to elicit adhesion, migration, or release of a bioactive molecule in the absence of an inhibiting compound for the particular barrier system being used. For example, a concentration of 1 μM fMLP may be used.

Measuring the inhibition of inflammatory cell activation can be achieved in several ways. The relative number of migrating PMN cells can be measured, for example, by a myeloperoxidase assay. The effect of cell activation, in the form of specific barrier dysfunction or abnormal electrolyte transport, can also be evaluated with electrophysiological measurements of the electrical resistance of the epithelial barrier, the electrical resistance of the epithelial cell membrane, and/or the endogenous cell current.

In a typical embodiment, the method would be a method of screening for a compound which modifies PMN adhesion to or migration across an intestinal epithelial barrier. This method comprises pretreating PMN with the compound, placing the pretreated PMN on one side of the intestinal barrier having a chemotactic agent on the other side, and determining whether the compound modifies PMN adhesion to or migration across the barrier. The epithelial barrier may be modeled by columnar epithelial cells with features similar to those of natural crypt epithelial, such as but not limited to a monolayer of human intestinal epithelial cell line T84. The chemotactic agent is fMLP (1 μM). The determination of the effectiveness of the compound is measured by the relative change in migration or adhesion of the PMN as measured by a myeloperoxidase assay. (Madara, J. L. et al. (1992) *J. Tiss. Cult. Meth.* 14:209-216.) Experimental details of this embodiment of the screening method are provided in Example 1 below.

This invention also provides a method of screening for a compound which attentuates the effect of an activated inflammatory cell upon a columnar epithelium, thereby attenuating one or more deleterious perturbations. This method comprises: combining an inflammatory cell with a prepared epithelial barrier, pretreating this combination with the compound, adding an activating agent, and determining whether the deleterious perturbations are attenuated by the compound.

The activating agent is an agent which stimulates the activation of the the inflammatory cell. Nonlimiting examples of an inflammatory cell activating agent are: phorbol ester, a $Ca^{+2}$ ionophore, phytohemaglutinin, chemotactic agents as described above, and endotoxin. In addition, the activating agent may have an effect on both the inflammatory cell and the epithelial cell. Nonlimiting examples of these kinds of activating agents are cytokines such as γ-IFN. The prepared epithelial barrier can be made as described above.

The attenuation can be measured in terms of electrical parameters such as the electrical resistance of the epithelial barrier, the electrical resistance of the epithelial cell membrane, or the endogenous current, or combinations thereof. The relative attenuation is the comparison of electrical parameters in the presence and absence of the compound.

A typical embodiment of this method will be used to screen for a compound which reduces or eliminates the symptoms of secretory diarrhea caused by abnormal chloride secretion. The PMN-derived paracrine factor that elicits chloride secretion from T84 intestinal epithelial cell monolayers is 5'-adenosine monophosphate (5'-AMP). (Madara, J. L. et al. (1993) *J. Clin. Invest.* 91: 2320-2325.) The method comprises: combining an intestinal epithelial barrier with PMN cells, stimulating chloride secretion by an intestinal epithelial cells with an amount of 5'-AMP or an agonist thereof; exposing the epithelial cells to the compound; and determining the attenuating effect of the compound upon the activation of the epithelial cells. The attenuation is measured by the electrical resistance of the epithelial barrier, the electrical resistance of the epithelial cell membrane, and/or the endogenous cell current.

Nonlimiting examples of 5'-AMP agonists are cyclic AMP, forskolin, and carbachol. Nonlimiting examples of variable ranges appropriate for a standard dose-response curve are: 5'-AMP ($10^{-8}$-$10^{-3}$ M, in the apical direction; $10^{-7}$-$10^{-2}$ M in the basal direction); cAMP and forskolin ($10^{-8}$-$10^{-2}$ M); and carbachol ($10^{-8}$-$10^{-3}$ M). For example, incremental steps of one-half log concentrations may be used. The amount of the 5'-AMP or agonist should be an amount sufficient to elicit intestinal chloride secretion. The following Example 2 discloses the experimental details for performing the electrophysiological measurements.

The intestinal epithelial barrier may be from, but is not limited to, any of the above mentioned intestinal cell lines, especially the T84 cell line. In addition, the screened compound may be, for example, an eicosanoid such as a lipoxin or lipoxin analog. The lipoxin analog may have a longer tissue half-life than the corresponding lipoxin, or may be actively absorbed by the intestine, or both.

Lipoxins, Lipoxin Analogs, and Combinations Thereof

Lipoxin compounds (e.g. natural lipoxins and lipoxin analogs) can be administered to a subject for the treatment or prevention of inflammation or inflammatory responses caused or contributed to by epithelial perturbations. Preferred lipoxin compounds are natural lipoxin $A_4$ (LXA$_4$) and analogs thereof.

"Natural lipoxins" are lipoxygenase-derived, biologically active eicosanoids produced by PMN, platelets, eosinophils and macrophages. (Samuelsson B., et al. (1987). *Science* 237: 1171-1176); (Dahlen S. E., and C. N. Serhan (1991). *In Lipoxygenases and Their Products*, Academic Press. New York, N.Y. 235-276). These compounds have been shown to elicit selective counterregulatory responses in human PMN in vitro, including the inhibition of leukotriene $B_4$ (LTB4) and fMLP-stimulated chemotactic responses across Boyden chambers (filters) (Lee T. H., et al. (1989). *Clin Sci* 77: 195-203); (Lee T. H., et al. (1991). *Biochem Biophys Res Comm* 180: 1416-1421), blocking of $Ca^{2+}$ mobilization (Springer T. A. (1990). *Nature* 346: 196-197), and inhibition of $LTD_4$-induced adhesion to mesangial cells (Brady H. R, et al. (1990). *Am. J. Physiol.* 259 (Renal Fluid Electrolyte Physiol. 28): F809-815). In vivo, lipoxins are potent inflammatory mediators which act to inhibit lymphocyte migration across vascular endothelia (Hedqvist P. J. et al. (1989). *Acta. Physiol Scand.* 137: 571-572), decrease $LTD_4$-induced vasoconstriction (Badr K. F., et al. (1989). *Proc. Nat Acad. Sci. U.S.A.* 86: 3486-3442), and modulate $LTD_4$-induced airway obstruction, (Christie P. E., et al. (1992) *Am Rev Respir Dis* 145: 1281-1284). Lipoxins include the bioactive (5S, 14R, 15S)-trihydroxy-6,10,12-trans-8-cis-eicosatetraenoic acid ($LXB_4$), and more preferably, (5S, 6R, 15S)-trihydroxy-7,9,13-trans-11-cis-eicosatetraenoic acid ($LXA_4$).

In addition to natural lipoxins, lipoxin analogs are useful antiinflammatory agents. "Lipoxin analogs" include compounds which are structurally similar to natural lipoxins, compounds which share the same receptor recognition site, compounds which share the same or similar lipoxin metabolic transformation region as lipoxin, and compounds which are art-recognized as being analogs of lipoxin. Lipoxin analogs also include metabolites of lipoxin and lipoxin analogs. A nonlimiting example of a lipoxin analog which inhibits PMN migration across an epithelial barrier is 11-trans-$LXA_4$. (See Example 1). Some lipoxin analogs are sufficiently lipophilic to be actively absorbed by the intestine. Generally, lipophilic analogs will have relatively short ($C_2$-$C_4$)hydrocarbon groups occupying the C-16+ position, as in the natural lipoxin compound.

One particularly suitable class of lipoxin analogs for use in the instant invention are those exhibiting a longer tissue half-life than corresponding natural lipoxins. A "lipoxin analog having a longer tissue half-life than corresponding lipoxins" refers to a compound which has an "active region" that functions like the active region of a natural lipoxin (e.g. $LXA_4$ or $LXB_4$), but which has a "metabolic transformation region" that differs from natural lipoxin. By "active region" is meant the region of a natural lipoxin or lipoxin analog, which is associated with in vivo cellular interactions. The active region may bind the "recognition site" of a cellular lipoxin receptor or a macromolecule or complex of macromolecules, including an enzyme and its cofactor. Preferred lipoxin $A_4$ analogs have an active region comprising C5-C15 of natural lipoxin $A_4$. Preferred lipoxin $B_4$ analogs have an active region comprising $C_5$-$C_{114}$ of natural lipoxin B4.

The term "metabolic transformation region" refers to that portion of a lipoxin, a lipoxin metabolite, or lipoxin analog including a lipoxin analog metabolite, upon which an enzyme or an enzyme and its cofactor attempts to perform one or more metabolic transformations which that enzyme or enzyme and cofactor normally-transform on lipoxins. The metabolic transformation region may or may not be susceptible to the transformation. A nonlimiting example of a metabolic transformation region of a lipoxin is a portion of $LXA_4$ that includes the C-13,14 double bond or the C-15 hydroxyl group, or both.

The pathway of lipoxin metabolism includes dehydrogenation, reduction of at least one unsaturated carbon-carbon bond, and/or ω-oxidation. These enzymatic transformation occur within the C-12 to C-20 portion of an $LXA_4$ analog, for example. Therefore, a lipoxin analog with a longer tissue half-life may be designed with chemical modifications which inhibit, resist, or raise the transition state energy of an analog or its metabolite for at least one of the metabolic transformations. Such analogs employ electronic effects at the relevant carbon atom, steric effects, and/or potential suicide substrate moieties such as those that allow covalent Michael addition to a metabolic enzyme.

Nonlimiting examples of a $LXA_4$ analog having a longer tissue half-life than $LXA_4$ include $LXA_4$ analogs with C-15 and/or C-16 substitutions such as: mono- or di-hydroxyl, methyl, fluoromethyl, and fluoro; C-16 substitutions such as phenyl, halo-substituted phenyl, and alkoxy; and C-19 or C-20 substitutions such as fluoromethyl, phenyl, and fluoro; and 13-yne or 14-yne substitutions. It is known that the intestine actively absorbs lipophilic fatty acids, especially those two to four carbon atoms in length. (Binder, H. J. In, *Gastrointestinal Disease*, 4th ed. (Sleisenger, M. H., and Fordtran, J. S., eds.) W. B. Saunders Co., Phildelphia, 1989, pp. 1022-1045.) In other embodiments, similar substitutions create structural analogs based on other lipoxins such as $LXB_4$.

In the most preferred embodiment of this invention, the compounds of this invention have the following structural formulas:

1

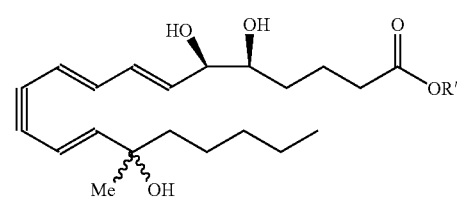

2

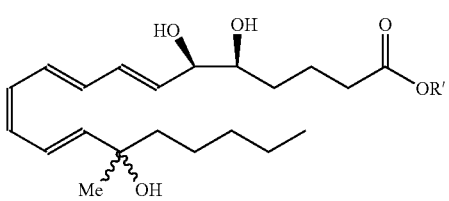

3

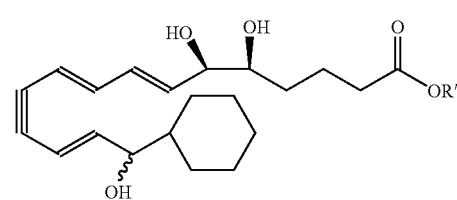

4

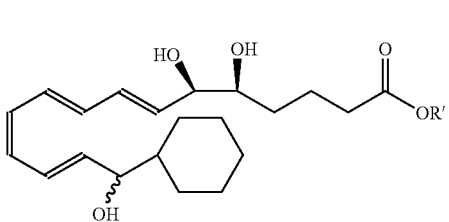

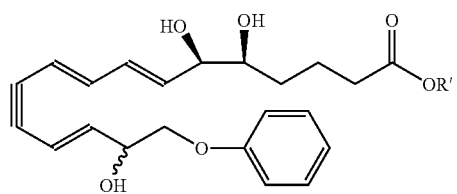
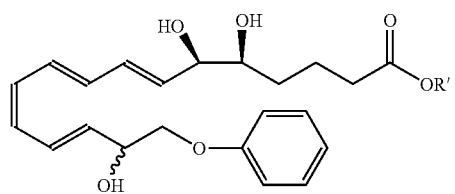
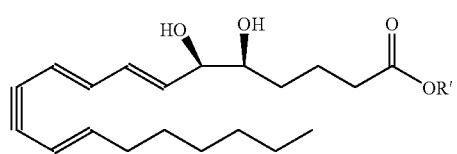
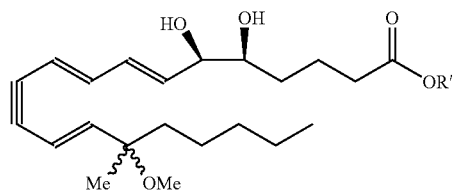
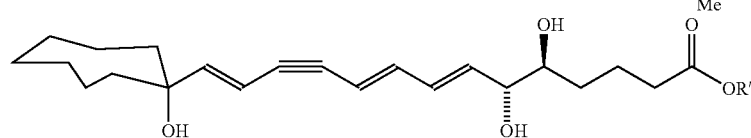
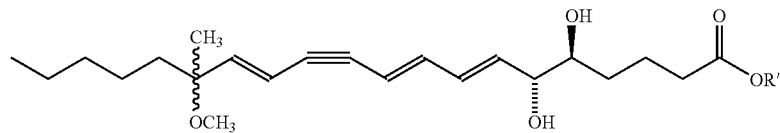
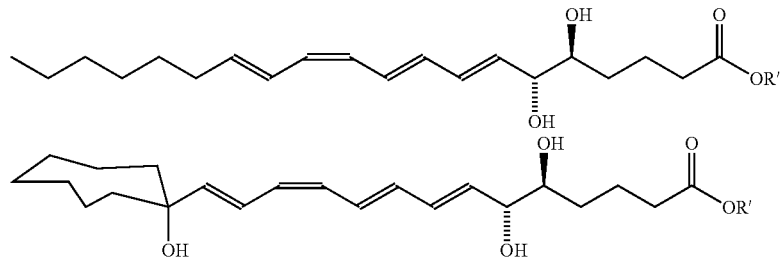
where R' is H or CH₃.
In other preferred embodiments of this invention, the compounds of this invention have the following structural formulas:
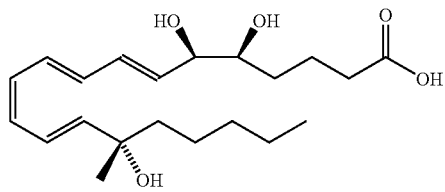
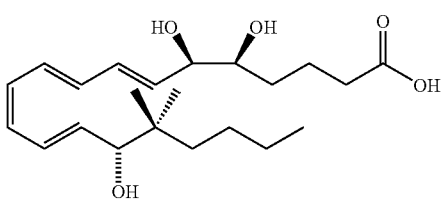
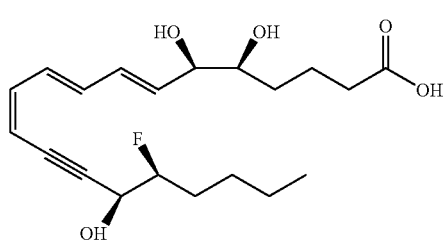
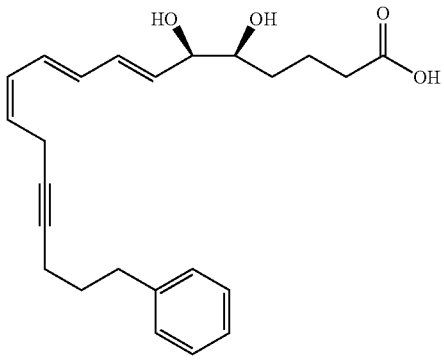

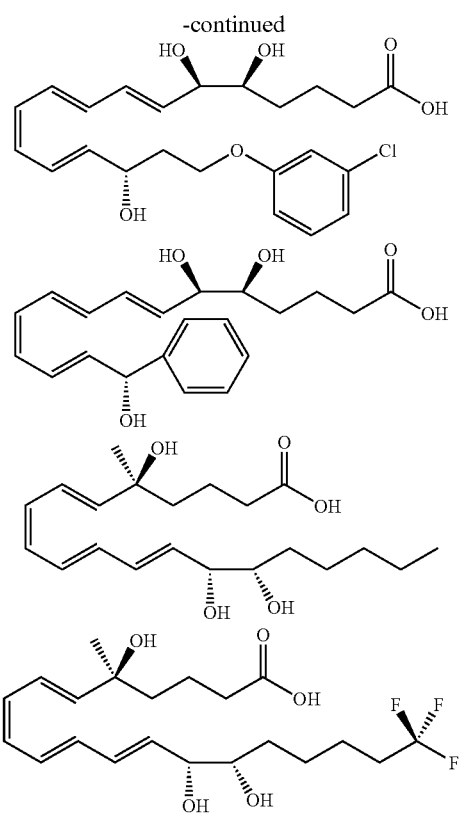

This invention also contemplates use of combinations of lipoxins and lipoxin analogs. A nonlimiting example of a combination is a mixture comprising a lipoxin analog x which inhibits one enzyme which metabolizes lipoxins and which optionally has specific activity with a lipoxin receptor recognition site, and a second lipoxin analogy which has specific activity with a lipoxin receptor recognition site and which optionally inhibits or resists lipoxin metabolism. This combination results in a longer tissue half-life for at least y since x inhibits one of the enzymes which metabolize lipoxins. Thus, the lipoxin action mediated or antagonized by y is enhanced.

Methods of Making Lipoxins and Lipoxin Analogs

Lipoxins may be isolated as described (Serhan, C. N. et al. (1990) *Methods in Enzymol.* 187: 167) from biological sources, synthesized or obtained commercially. $LXA_4$ and $LXB_4$ are available from Biolmol, Inc. (Philadelphia, Pa.) and Cayman Biochemical (Ann Arbor, Mich.). $LXA_4$, $LXB_4$, and the 11-trans-$LXA_4$ isomer are available from Cascade Biochemical, Ltd (Berkshire, UK). Nonlimiting examples of the structures and syntheses of both lipoxins and lipoxin analogs, including methyl esters of lipoxin analogs, are illustrated in the following patents and publications:

(1) Nicolaou, K. C. et al. Identification of a novel 7-cis-11-trans-$LXA_4$ generated by human neutrophils: total synthesis, spasmogenic activities and comparison with other geometric isomers of lipoxins $A_4$ and $B_4$ (1989). *Biochim. Biophys. Acta* 1003:44-53;

(2) Nicolaou, K. C. et al. Total synthesis of novel geometric isomers of $LXA_4$ and $LXB_4$ (1989). *J. Org. Chem.* 54: 5527-5535;

(3) Nicolaou, K. C. et al. Lipoxins and related eicosanoids: biosynthesis, biological properties, and chemical synthesis (1991). *Angew. Chem. Int. Ed. Engl.* 30: 1100-1116;

(4) U.S. Pat. Nos. 4,576,758; 4,560,514; 5,079261; and 5,049,681; and (5) JP Patent Nos. 3,227,922; 63,088,153; 62,198,677; and 1,228,994.

Preferred lipoxin analogues having a longer half-life than natural lipoxins can be prepared as described in the following Example 2

Methods of Treatment

This invention provides, in part, method of treating or preventing inflammation or an inflammatory response caused or contributed to by the activation of inflammatory cells which interact with a columnar epithelium. The interaction between activated inflammatory cells and the epithelium results in one or more epithelial perturbations. This anti-inflammatory treatment is the administration to a subject of an effective amount of a lipoxin, lipoxin analog, or combination thereof to inhibit the activation of the inflammatory cell such that the epithelial perturbation and inflammation or an inflammatory response are significantly reduced or eliminated.

A significant reduction of inflammation or an inflammatory response includes reducing or eliminating one or more of the symptoms associated with inflammation. For example, PMN transmigration stimulates electrogenic chloride secretion, which is the basis of secretory diarrhea, one of the symptoms of inflammatory bowel diseases. (Nash, S. et al. (1991). *J. Clin. Invest* 87: 1474-1477.) Additional nonlimiting examples of symptoms of inflammatory bowel diseases are cramping abdominal pain, malabsorption, dehydration, bloody stool, or fever. In addition to the inflammatory bowel disease listed above, bowel inflammation may also result from surgery, allergy, chemical exposure, or physical injury. Reduction of epithelial perturbation can also include inhibition of inflammatory cell activation. For example, a reduced perturbation can be the inhibition of PMN migration in the basal-to-apical direction represented by a decrease of at least about 25%.

Lipoxins include $LXA_4$ or $LXB_4$. The lipoxin analog can have a longer tissue half-life than the corresponding natural lipoxin. The lipoxin analog can also be lipophilic. The lipoxin analog can also be actively absorbed by the intestine. Lipoxins, lipoxin analogs, and combinations of lipoxins as used in these methods of treatment are defined above in the preceding two sections.

This invention also provides a method for the treatment or prevention of one or more of the symptoms of inflammatory diseases of columnar epithelia. In this method, the epithelial perturbations which cause or contribute to these symptoms may or may not be mediated by inflammatory cells. This method of treatment comprises the administration to a subject of an effective amount of a lipoxin, lipoxin analog, or combination thereof such that the epithelial inflammation or inflammatory response is significantly reduced or eliminated.

A significant reduction of inflammation or an inflammatory response includes reducing or eliminating one or more of the symptoms associated with inflammation. For example, abnormal chloride secretion causes or contributes to secretory diarrhea, a symptom of inflammatory bowel diseases. 5'AMP elicits chloride secretion from T84 intestinal epithelial cell monolayers, in a manner which may not always be dependent upon PMN. (Madara, J. L. et al. (1993) *J. Clin. Invest* 91:2320-2325.) Additional nonlimiting examples of symptoms of inflammatory bowel diseases are cramping abdominal pain, malabsorption, dehydration, bloody stool, or fever.

Lipoxins include $LXA_4$ or $LXB_4$. The lipoxin analog may have characteristics such as a longer tissue half-life than the corresponding natural lipoxin, be lipophilic, or be actively absorbed by the intestine, or a combination thereof. Lipoxins, lipoxin analogs, and combinations of lipoxins as used in these methods of treatment are defined above.

In one embodiment, the lipoxin or lipoxin analog independently acts to modulate epithelial perturbations, such as chloride ion secretion. Without intending to be bound, it is speculated that lipoxins and lipoxin analogs, independent of PMN activation, can decrease chloride ion secretion to an extent that secretory diarrhea is significantly reduced.

Pharmaceutical Compositions and Packaged Drugs

This invention also encompasses pharmaceutical compositions and packaged drugs containing lipoxins, lipoxin analogs, salts thereof, and combinations thereof for the treatment of inflammation and inflammatory responses in a subject. In one embodiment of this invention, the pharmaceutical compositions and packaged drugs are for the treatment or prevention of the columnar epithelial perturbations related to PMN activation in inflammatory bowel diseases.

The term "subject" is intended to include living organisms susceptible to conditions or diseases caused or contributed to by inflammation and inflammatory-responses. Examples of subjects include humans, dogs, cats, cows, goats, and mice. The term "subject" is further intended to include transgenic species.

The term "pharmaceutically acceptable salt" is intended to include art-recognized pharmaceutically acceptable salts. These non-toxic salts are usually hydrolyzed under physiological conditions, and include organic and inorganic bases. Examples of salts include sodium, potassium, calcium, ammonium, copper, and aluminum as well as primary, secondary, and tertiary amines, basic ion exchange resins, purines, piperazine, and the like. The term is further intended to include esters of lower hydrocarbon groups, such as methyl, ethyl, and propyl. In this paragraph, the next paragraph, and in the discussion of methods of treatment and pharmaceutical compositions, it should be understood that references to lipoxin analogs are meant to include corresponding pharmaceutically acceptable salts.

The term "pharmaceutical composition" comprises one or more natural lipoxin or lipoxin analog as an active ingredient(s), or a pharmaceutically acceptable salt(s) thereof, and may also contain a pharmaceutically acceptable carrier and optionally other therapeutic ingredients. The compositions include compositions suitable for oral, rectal, ophthalmic, pulmonary, nasal, dermal, topical, parenteral (including subcutaneous, intramuscular and intravenous) or inhalation modes of administration. The most suitable route in any particular case will depend on the nature and severity of the conditions being treated and the nature of the active ingredient(s). The compositions may be presented in unit dosage form and prepared by any of the well-known methods.

Appropriate dosage regimes for treating a particular disease or condition associated with columnar epithelial inflammation can be determined empirically by one of skill in the art and may be adjusted for the purpose of improving the therapeutic response. For example, several divided dosages may be administered daily or the dose may be proportionally reduced over time. A person skilled in the art normally may determine the effective dosage amount and the appropriate regime. A less potent lipoxin analog composition may be selected to treat mild or highly localized inflammation, while a larger dosage or more potent lipoxin analog may be selected to treat severe or widespread inflammatory episodes. An "effective anti-inflammatory amount" of a lipoxin containing pharmaceutical composition for treating a disease or condition associated with a columnar epithelial inflammation shall mean that amount that ameliorates the inflammation and eliminates the syptoms of the disease. An "effective anti-diuretic amount" of a lipoxin containing pharmaceutical composition is that amount that restores transportation of fluid, electrolytes, or nutrients by a columnar epithelium to the normal, homeostatic level.

The term "packaged drug" is meant to include one or more dosages of an effective pharmaceutical composition of a lipoxin, a lipoxin analog, salt thereof or combination thereof, a container holding the dosage(s), and instructions for administering the dosage(s) to a subject for treatment or prevention of inflammation or an inflammatory response.

The present invention is further illustrated by the following example which should in no way be construed as being further limiting. The contents of all references and issued patents cited throughout all portions of this application including the background are expressly incorporated by reference.

EXAMPLE 1

Lipoxin $A_4$ M Dulates Migration of Human PMNs Across Intestinal Epithelial Monolayers.

Lipoxins Synthetic $LXA_4$, $LXB_4$, and 11-trans-$LXA_4$ were obtained from Cascade Biochem Ltd. (Berkshire, United Kingdom). Concentrations were determined from extinction coefficients as described in Sheppard K-A., et al. (1992). *Biochimica et Biophysica Acta* 1133: 223-234. All eicosanoid stock solutions were stored at −70° C. in methanol (American Scientific Products). Eicosanoids were diluted in modified HBSS to a concentration of 1 µM prior to all experiments. PMN or T84 monolayers were exposed to lipoxins at indicated concentrations and allowed to incubate at 37° C. for the indicated period of time. Vehicle controls consisted of dilutions of the solvent (ethanol) equivalent to the highest concentration of lipoxin used in any given experiment (0.01%).

Cell culture Approximately 350 epithelial monolayers were used for these studies. T84 intestinal epithelial cells (passages 70-95) were grown and maintained as confluent monolayers on collagen coated permeable support. Monolayers were grown on 0.33 $cm^2$ ring-supported polycarbonate filters (Costar Corp., Cambridge, Mass.) and utilized 6-14 days after plating as described in Example 2. Transepithelial resistance to passive ion flow was measured as described in Parkos C. A., et al. (1991). *J. Clin. Invest.* 88: 1605-1612); and Parkos C. A., et al. (1992). *J. Cell. Biol.* 117: 757-764). Inverted monolayers used to study migration of PMN in the basolateral-to-apical direction were constructed as described in Parkos C. A., et al. (1991). *J. Clin. Invest.* 88:1605-1612).

Migration assay: The PMN transepithelial migration assay has been detailed in Nash S., et al. (1987). *J. Clin. Invest.* 80: 1104-1113; Nash S., et al. (1991). *J. Clin. Invest* 87: 1474-1477); Parkos C. A., et al. (1991). *J. Clin. Invest.* 88: 1605-1612); and Parkos C. A., et al. (1992). *J. Cell. Biol.* 117: 757-764. Briefly, human PMN were isolated from normal human volunteers and suspended in modified HBSS (without $Ca^{2+}$ and $Mg^{2+}$, with 10 mM Hepes, pH 7.4, Sigma) at a concentration of $5 \times 10^7$/ml. Prior to addition of PMN, T84 monolayers were extensively rinsed in HBSS to remove residual serum components. Migration assays were performed by the addition of PMN (40 µl) to HBSS (160±1) in the upper chambers after chemoattractant (1 µM fMLP in HBSS) was added to the opposing (lower) chambers. Unless otherwise indicated, PMN were not washed free of $LXA_4$ prior to addition to monolayers, and therefore, a five-fold dilution of lipoxin was present during the migration assay. For apical-to-basolateral migration experiments, PMN ($2\times10^6$) were added at time 0. Migration in the basolateral-to-apical direction, while qualitatively similar, is substantially more efficient than in the apical-to-basolateral direction. (Parkos C. A., et al. (1991). *J. Clin. Invest.* 88: 1605-1612). Therefore, 5-fold fewer PMN ($4\times10^5$) were added when migration proceeded in the basolateral-to-apical direction in order that baseline migration signals be approximately equivalent in both directions. (Parkos C. A., et al. (1991). *J. Clin. Invest.* 88: 1605-1612). Migration was allowed to proceed for 120 minutes, unless otherwise noted. All PMN transepithelial migration experiments were performed in a 37° C. room to ensure that epithelial monolayers, solutions, plasticware, etc., were maintained at uniform 37° C. temperature.

When used, inhibitors to cyclooxygenase (indomethacin, Sigma), leukotriene biosynthesis (MK886, a kind gift from Merck Frosst), G-proteins (pertussis toxin, Calbiochem), or protein kinase C(H7, Sigma; staurosporine, Sigma) were pre-incubated with PMN at indicated concentrations for 15 min at 37° C. Inhibitors were washed free from PMN by two washes with HBSS. PMN were subsequently exposed to $LXA_4$ (10 nM) and PMN transepithelial migration was assessed as described above in the apical-to-basolateral direction.

Migration was quantitated by assaying for the PMN azurophilic granule marker myeloperoxidase (MPO) as described previously (Parkos C. A., et al. (1991). *J. Clin. Invest* 88: 1605-1612). Following each migration assay, non-adherent PMN were extensively washed from the surface of the monolayer and PMN cell equivalents (PMN CE), estimated from a standard curve, were assessed as the number of PMN's associated with the monolayer, the number which had completely traversed the monolayer (ie. across the monolayer into the reservoir bath), as well as the total number of transmigrating PMN (the sum of monolayer and reservoir-associated PMN).

Data Presentation: Individual experiments were performed using large numbers of uniform groups of monolayers and PMN from individual blood donors on individual days. PMN isolation was restricted to five different blood donors (repetitive donations) over the course of these studies. Myeloperoxidase assay data were compared by two-factor analysis of variance (ANOVA) or by comparison of means using Student's t-Test PMN migration results are represented as PMN CE derived from a daily standard PMN dilution curve. Monolayer-associated PMN are represented as the number of PMN CE per monolayer and reservoir-associated PMN (ie. PMN which had completely traversed the monolayer into the lower chamber) are represented as the number of PMN CE/ml (total volume of 1 ml). Values are expressed as the mean and s.e.m. of n experiments.

Results:

$LXA_4$ Exposure to T84 Epithelial Monolayers does not Alter Subsequent fMLP-Induced PMN Migration.

PMN can be induced to transmigrate across T84 epithelial monolayers in response to a transepithelial gradient of the chemotactic peptide fMLP (1 µM). (Nash S., et al. (1987). *J. Clin. Invest* 80: 1104-1113); (Parkos C. A., et al. (1991). *J. Clin. Invest.* 88: 1605-1612). To determine whether $LXA_4$ exposure to $T_{84}$ intestinal epithelial cells influenced subsequent PMN migration, epithelial cell monolayers were incubated with $LXA_4$ at a concentration 10 nM for 15 min at 37° C. (conditions which elicit significant effects when PMN's are pre-exposed to $LXA_4$, see below), with and without removal of $LXA_4$ from monolayers, followed by addition of untreated PMN's under chemotactic conditions. In these experiments, PMN migration across T84 monolayers exposed to $LXA_4$ did not differ from vehicle control ($14.8\pm1.4$ vs $15.7\pm1.8\times10^4$ PMN CE/ml for control and $LXA_4$ exposed monolayers, n=6 each, n.s.). Removal of $LXA_4$ from monolayers by washing thrice with HBSS prior to addition of PMN had no apparent effect on the total number of transmigrating PMN ($14.3\pm1.1\times10^4$ PMN CE/ml, n=6, n.s. compared to either control or $LXA_4$ exposed monolayers).

In addition, exposure of intestinal epithelial cells to $LXA_4$ did not significantly influence the integrity of T84 epithelial monolayers. To examine this, transepithelial resistance to passive ion flow was assessed prior to, and after addition of 10 nM $LXA_4$ to T84 intestinal epithelial monolayers for 2 hrs (simulated conditions for entire migration assay period). During this period, transepithelial resistance did not significantly decrease following addition of $LXA_4$ (baseline resistance $1255\pm56$ ohm-$m^2$ and $1089\div108$ ohm-$cm^2$ after 2 hr, n=8, n.s.). These results suggest that monolayer integrity, as assessed by transepithelial resistance, was not affected by $LXA_4$ treatment and that epithelial pre-exposure to $LXA_4$ has no subsequent effect on fMLP-induced PMN migration.

$LSA_4$ does Not Stimulate Migration.

To investigate whether $LXA_4$ could serve to stimulate PMN migration in this assay system, dilutions of $LXA_4$ in the range of 0.01-10 nM were placed in the lower chamber of migration wells. Untreated PMN's were added to the upper chamber and assessed for chemotactic capacity toward $LXA_4$ in the apical-to-basolateral direction. $LXA_4$ was no more effective than HBSS in promoting PMN migration; compared to fMLP (1 µM), PMN migration toward $LXA_4$ resulted in a total of $6\pm2.1$, $9\pm3.6$, $6\pm2.4$, and $12\pm1.4\%$ of fMLP-induced PMN migration for 0.01, 0.1, 1.0, and 10 nM $LXA_4$, respectively. In the absence of a chemotactic gradient (HBSS), $10\pm2.9\%$ of fMLP-induced migration occurred. These results indicate that $LXA_4$, in the concentrations tested, did not stimulate PMN transepithelial migration.

Pre-Exposure of PMN to $LXA_4$ Enhances fMLP-Induced PMN Migration in the Apical-to-Basolateral Direction.

To determine if PMN exposure to $LXA_4$ alters subsequent fMLP-induced migration, PMN were incubated 10 nM $LXA_4$ for 15 minutes, then added directly to the apical surface of T84 epithelial monolayers, and subsequently assessed for their ability to traverse T84 epithelial monolayers using a myeloperoxidase assay. (Parkos C. A., et al. (1991). *J. Clin. Invest* 88: 1605-1612). PMN ($5\times10^7$/ml)-were pre-incubated with 10 nM $LXA_4$ for 15 min. at 37° C. and layered on the apical surface of washed T84 epithelial monolayers at a density of $2\times10^6$/monolayer. PMN were driven to transmigrate basolaterally under the influence of a 1 µM gradient of fMLP.

Results were obtained by harvesting the PMN specific enzyme myeloperoxidase (MPO) from washed monolayers, lower reservoirs and total MPO activity after 120 min, relative to a known standard number of PMN. Since tight junctions are the rate limiting barrier to passive paracellular permeation, transmigration is defined as movement of PMN across the tight junction. Since monolayer-associated PMN were largely below the tight junction (see results), total transmigration in the apical-to-basolateral direction equals the sum of PMN in the opposite reservoir plus monolayer PMN. Data are pooled from 9 individual monolayers in each condition and results are expressed as the mean and SEM.

PMN pre-exposure to $LXA_4$ resulted in significantly increased PMN transepithelial migration in the apical-to-basolateral direction. Increased PMN migration was evident in both monolayer-associated PMN numbers ($2.98\pm0.57$ vs. $6.93\pm1.77\times10^4$ PMN CE/monolayer for vehicle control and $LXA_4$ exposed PMN, respectively, $p<0.001$), as well as the number of PMN which completely traversed the epithelial monolayer ($6.61\pm0.50$ vs. $11.02\pm2.91\times10^4$ PMN CE/ml for vehicle control and $LXA_4$ exposed, respectively, $p<0.01$), resulting in a nearly 2-fold increase in the total number of transmigrating PMN ($9.58\pm1.05\times10^4$ PMN CE/ml for vehicle control and $17.95\pm2.15\times10^4$ PMN CE/ml for $LXA_4$ pre-exposed PMN, p<0.01). As reported previously, (Parkos C. A., et al. (1991). *J. Clin. Invest* 88: 1605-1612), examination of 1 µm T84 epithelial monolayer sections have revealed that PMN are only rarely associated with the apical epithelial surface and the majority of monolayer associated PMN are found subjunctionally, indicative of migration. Therefore, monolayer-associated PMN in this apical-to-basolateral assay are considered transmigrated across the tight junction, the rate limiting barrier in PMN transepithelial migration. (Parkos C. A., et al. (1991). *J. Clin. Invest*. 88: 1605-1612).

To further characterize this transmigratory event, PMN were pre-exposed to $LXA_4$ (10 nM) for various periods of time and subsequently assessed for their ability to transmigrate across T84 epithelial monolayers in the apical-to-basolateral direction. PMN ($5\times10^7$/ml) were pre-incubated with 10 nM $LXA_4$ for various periods of time in the range of 0-60 min at 37° C. or pre-incubated with various indicated concentrations of $LXA_4$ for 15 min. at 37° C. and layered on the apical surface of washed T84 epithelial monolayers at a density of $2\times10^6$/monolayer. PMN were driven to transmigrate basolaterally under the influence of a 1 µM gradient of fMLP. Results were again obtained by harvesting the PMN specific enzyme myeloperoxidase (MPO) from washed monolayers, lower reservoirs and total MPO activity after 120 min, relative to a known standard number of PMN. Data are pooled from 7-10 individual monolayers in each condition and results are expressed as the mean and SEM.

Pre-exposure of PMN to $LXA_4$ resulted in increased total PMN migration after a $LXA_4$ pre-exposure period of 5-30 min. (compared to vehicle controls, for PMN's pre-exposed to 10 nM $LXA_4$, migration increased by 50, 68 and 51% at 5, 15 and 30 min. exposure times, respectively, all p<0.025). Migration had returned to vehicle control values by 45 and 60 minutes of PMN pre-exposure to $LXA_4$. Pre-exposure of PMN to $LXA_4$ was found to be a necessary prerequisite for $LXA_4$ action on stimulating PMN migration. Indeed, exposure of PMN's to 10 nM $LXA_4$ immediately prior to their addition to epithelial monolayers (ie. 0 min. pre-exposure) resulted in no effect on subsequent fMLP-induced PMN migration ($16.34\pm4.07$ vs. $16.61\pm3.56\times10^4$ total PMN CE/ml for vehicle control and $LXA_4$ pre-exposure for 0 min., respectively, n.s.). The $LXA_4$ pre-exposure time-dependent enhancement of subsequent neutrophil migration was largely due to reservoir-associated PMN ($11.06\pm3.05$ vs $18.02\pm3.35$, $19.96\pm3.18$, $19.64\pm3.54\times10^4$ PMN CE/ml for vehicle control and PMN $LXA_4$ pre-exposure times of 5, 15 and 30 minutes, respectively, two-factor ANOVA p<0.01). However, a significant increase in the number of monolayer-associated PMN occurred at 15 minutes of $LXA_4$ pre-exposure ($4.17\pm1.17$ for vehicle control vs $7.55\pm0.71\times10^4$ PMN CE/monolayer for PMN's exposed to 10 nM $LXA_4$, p<0.01).

The effect of $LXA_4$ pre-exposure to PMN and subsequent PMN transepithelial migration in the apical-to-basolateral direction was found to be concentration dependent Pre-exposure of PMN to $LXA_4$ concentrations in the range of 1.0 pM-10 nM for 15 minutes at 37° C. elicited increased PMN migration at doses of 0.1, 1.0 and 10 nM final concentrations. Similar to the time-course data presented above, $LXA_4$-elicited stimulation of PMN migration was manifest as an increase in the number of PMN in lower reservoirs ($11.06\pm3.05$ vs $20.38\pm4.83$, $19.96\pm4.83$, $15.43\pm4.65$, $14.11\pm3.01$, and $13.71\pm4.14\times10^4$ PMN CE/ml for vehicle control and PMN $LXA_4$ pre-exposure doses of 10, 1, 0.1, 0.01, and 0.001 nM, respectively, for 15 min., 37° C., two-factor ANOVA, p<0.025).

To determine whether the stimulatory action of $LXA_4$ was present throughout the incubation period, PMN's were pre-exposed to $LXA_4$ (10 nM, 15 min), layered on the apical surface of T84 monolayers and driven to transmigrate basolaterally. Monolayers were harvested at various time points during migration and assayed for PMN by myeloperoxidase content. PMN ($5\times10^7$/ml) were pre-incubated with 10 nM $LXA_4$ for 15 min. at 37° C. and layered on the apical surface of washed T84 epithelial monolayers at a density of $2\times10^6$/monolayer. PMN were driven to transmigrate basolaterally under the influence of a 1 µM gradient of fMLP.

Results were obtained by assaying the PMN specific enzyme myeloperoxidase (MPO), relative to a known standard number of PMN. Total MPO activity (including reservoir- and monolayer-associated MPO activity) was tested. Data were pooled from 6 individual monolayers in each condition and results were expressed as the mean and SEM.

The stimulatory effect of $LXA_4$ on PMN migration in the apical-to-basolateral direction was present by 45 min after addition of PMN ($0.06\pm0.04$ vs $1.51\pm0.12\times10^4$ PMN CE/ml for vehicle control and PMN exposed to $LXA_4$, respectively, p<0.05), and was maintained throughout the 135 min experimental period (two-factor ANOVA, p<0.01).

To assess whether pre-exposure of PMN to $LXA_4$ was reversible, PMN were incubated with 10 nM $LXA_4$ for 15 minutes, washed twice in $Ca^{2+}$- and $Mg^{2+}$-free HBSS, and assessed for their ability to migrate across monolayers of T84 epithelial cells in the apical-to-basolateral direction. Here, PMN exposed to $LXA_4$ did not differ from control in their ability to migrate across T84 epithelial monolayers ($14.1\pm0.4$ vs $14.5\pm0.3\times10^4$ PMN CE/ml for control and $LXA_4$ exposure followed by washout, respectively, n=6 each, n.s.). In the presence of $LXA_4$, a total of $18.6\pm1.0\times10^4$ PMN CE/ml migrated (n=6, p<0.025 compared to control and washout control), suggesting that $LXA_4$-induced enhancement of PMN migration in the apical-to-basolateral direction requires the presence of $LXA_4$.

A final determination was whether PMN-conditioned $LXA_4$ and epithelial-conditioned $LXA_4$ maintained its ability to enhance PMN migration in the apical-to-basolateral direction. Samples of $LXA_4$ (10 nM) were incubated with either PMN or T84 epithelial cells for 15 or 45 minutes. Supernatants were harvested and subsequently exposed to PMN for 15 min and added to the apical surface of T84 monolayers under transmigratory conditions (1 µM fMLP trasepithelial gradient) for 2 hrs at 37° C. Compared to PMN pre-exposed to HBSS ($11.3\pm2.2\times10^4$ total PMN CE/ml), PMN pre-exposed to PMN-conditioned $LXA_4$ (15 min) resulted in a total PMN migration $18.0\pm2.1\times10^4$ PMN CE/ml (n=3, p<0.05 compared to control). PMN pre-exposed to epithelial-conditioned $LXA_4$ (15 min) resulted in a total PMN migration $16.8\pm3.3\times10^4$ PMN CE/ml (n=3, p<0.05 compared to control). Supernatants from PMN-conditioned $LXA_4$ (45 min) were not effective in enhancing PMN migration in the apical-to-basolateral direction ($12.36\pm3.1\times10^4$ total PMN CE/ml compared to HBSS control of $14.3\pm3.2\times10^4$ total PMN CE/ml, n—3, p=n.s.). These results suggest that enhancement of PMN migration in the apical-to-basolateral direction involves a step which is subsequent to PMN pre-incubation with $LXA_4$.

PMN Pre-Exposure to $LXA_4$ Decreases fMLP-Induced PMN Migration in the Basolateral-to-Apical Direction.

Quantitative as well as qualitative differences can exist in PMN tansepithelial migration depending on the direction of migration. To investigate the effect of $LXA_4$ on the polarity of migration, inverted monolayers (which permit basolateral-to-apically directed migration) were prepared.

PMN ($1 \times 10^7$/ml) were pre-incubated with 10 nM LXA$_4$ for 15 min. at 37° C. and layered on the basolateral surface of washed T84 epithelial monolayers (i.e. inverted monolayers) at a density of $4 \times 10^5$/monolayer. PMN were driven to transmigrate apically under the influence of a 1 µM gradient of fMLP.

Results were obtained by harvesting the PMN specific enzyme myeloperoxidase (MPO) from lower reservoirs and washed monolayers after 120 min, relative to a known standard number of PMN. Since tight junctions are the rate limiting barrier to passive paracellular permeation, trasmigration is defined as movement of PMN across the tight junction. Since monolayer-associated PMN were largely below the tight junction, total transmigration in the basolateral-to-apical direction equates with PMN in the opposite reservoir only. Data were pooled from 9 individual monolayers in each condition and results were expressed as the mean and SEM.

Pre-exposure of PMN to LXA$_4$ (10 nM) for 15 minutes markedly decreased PMN migration in the basolateral-to-apical direction. Unlike the results found in the apical-to-basolateral direction, migration of PMN's in this physiologically relevant direction was significantly decreased compared to vehicle controls ($28.02 \pm 3.08$ vs $18.77 \pm 1.48 \times 10^4$ PMN/ml for control and PMN pre-exposed to 10 nM LXA$_4$ for 15 min, respectively, $p<0.01$). Migration in the basolateral-to-apical direction resulted in no significant difference in the number of monolayer-associated PMN's following pre-exposure to LXA$_4$ ($2.01 \pm 0.20$ vs $2.00 \pm 0.31$ for control and PMN exposed to LXA$_4$, respectively, p=n.s.). This polarized action of LXA$_4$ was confirmed by performing parallel apical-to-basolateral and basolateral-to-apical migration experiments using T84 cells from the same plating and same passage and using PMN from the same donors on three separate occasions.

A time course of LXA$_4$ pre-exposure to PMN was next performed for basolateral-to-apical directed migration. PMN ($1 \times 10^7$/ml) were pre-incubated with various indicated concentrations of LXA$_4$ for 15 min. at 37° C. and layered on the basolateral surface of washed T84 epithelial monolayers at a density of $^4 \times 10^5$/monolayer. PMN were driven to transmigrate basolaterally under the influence of a 1 µM gradient of fMLP.

Results were obtained by harvesting the PMN specific enzyme myeloperoxidase (MPO) from lower reservoirs and washed monolayers after 120 min, relative to a known standard number of PMN. Data were pooled from 9-12 individual monolayers in each condition and results are expressed as the mean and SEM.

Similar to the apical-to-basolateral direction, decreased transepithelial migration was present at 15 minutes of PMN pre-exposure to 10 nM LXA$_4$ ($11.07 \pm 1.83$ for control vs. $6.29 \pm 1.21 \times 10^4$ PMN/ml, $p<0.01$). No differences in the number of monolayer-associated PMN were present at any period of LXA$_4$ exposure. Dose-response experiments (all 15 min. pre-exposure) revealed that pre-exposure of PMN to 10 and 1 nM LXA$_4$ resulted in a significantly reduced number of transmigrating PMN in the basolateral-to-apical direction ($11.07 \pm 1.83 \times 10^4$ PMN/ml for control samples vs $6.29 \pm 1.21$ and $6.99 \pm 1.33 \times 10^4$ PMN/ml following pre-exposure to 10 and 1 nM LXA$_4$, respectively, both $p<0.025$). Again, this diminished transmigratory response in the basolateral-to-apical direction was associated with reservoir-associated PMN only, with no apparent effect on the number of monolayer-associated PMN.

It was also determined whether PMN-conditioned LXA$_4$ or epithelial-conditioned LXA$_4$ were effective in decreasing PMN migration in the basolateral-to-apical direction. Similar to the results in the apical-to-basolateral direction (see above), PMN pre-exposed to either PMN-conditioned LXA$_4$ ($8.07 \pm 1.63$ vs. buffer control $13.18 \pm 1.91 \times 10^4$ PMN/ml, n=4, $p<0.025$) or epithelial-conditioned LXA$_4$ ($9.01 \pm 1.76$ compared to buffer control of $14.23 \pm 2.06 \times 10^4$ PMN/ml, n=4, $p<0.04$) maintained activity which decreased PMN transepithelial migration in the basolateral-to-apical direction.

Pre-Exposure of PMN to Structurally Related Lipoxins

To investigate the specificity of LXA$_4$ causing decreased migration in the physiological direction, the effects of PMN exposure to LXB$_4$ and 11-trans-LXA$_4$ were also examined. PMN ($1 \times 10^7$/ml) were pre-incubated with 10 nM LXA$_4$, LXB$_4$ or 11-trans-LXA$_4$ for 15 min. at 37° C. and layered on the basolateral surface of washed T84 epithelial monolayers (i.e. inverted monolayers) at a density of $4 \times 10^5$/monolayer. PMN were driven to transmigrate apically under the influence of a 1 µM gradient of fMLP. Results were obtained by harvesting the PMN specific enzyme myeloperoxidase (MPO) after 120 min, relative to a known standard number of PMN. Total MPO activity (including reservoir- and monolayer-associated MPO activity) was expressed as the percent PMN migration inhibition. Data were pooled from 7 individual monolayers in each condition and results were expressed as the mean and SEM. Pre-exposure of PMN's to 10 nM LXB$_4$, 11-trans-LXA$_4$ produced a $7 \pm 4\%$ (p=n.s. compared to vehicle control) and $16 \pm 6\%$ ($p<0.05$) inhibition of PMN migration, respectively, while LXA$_4$ inhibited migration by $28 \pm 4\%$ ($p<0.01$). These observations suggest structural specificity for LXA$_4$.

Effect of Inhibitors on LXA-Elicited Enhancement of PMN Transepithelial Migration in the Apical-to-Basolateral Direction.

To determine whether LXA$_4$-induced modulation of PMN migration could be pharmocologically altered, a series of experiments were done in which PMN were exposed to specific inhibitors, washed free of inhibitor and subsequently assayed for the LXA$_4$ effect on PMN transepithelial migration in the apical-to-basolateral direction.

Pre-exposure of PMN to indomethacin (50 µM, 15 min, 37° C.), a cyclooxygenase inhibitor, (Smolen J. E., and G. Weissman (1980). *Biochem. Pharmacol.* 29: 533-538), did not effect baseline PMN migration in the presence of a transepithelial gradient of fMLP ($109 \pm 13\%$ vehicle control, n=6, p=n.s. compared to untreated control). Likewise, pre-exposure of PMN to indomethacin followed by exposure to LXA$_4$ (10 nM) did not alter the LXA$_4$-elicited increase in fMLP driven PMN migration in the apical-to-basolateral direction ($61 \pm 11\%$ increase vs $54 \pm 7\%$ increase over control for LXA$_4$ treated PMN with and without indomethacin, respectively, p=n.s.). Likewise, PMN pre-treatment with the compound MK886 (10 ng/ml), a specific inhibitor of leukotriene generation, (Gillard J., et al. (1989). *Can. J. Physiol. Pharmacol.* 67: 456-464), did not alter baseline fMLP driven PMN migration and did not effect the LXA$_4$-elicited increase in PMN transepithelial migration.

Staurosporine, a potent inhibitor of protein kinase C (PKC), (Sako T., et al. (1988). *Cancer Res.* 48: 4646-4650), was assessed for its ability to inhibit the LXA$_4$ effect. Interestingly, staurosporine alone (10 nM final concentration) was found to inhibit PMN transepithelial migration ($93 \pm 5\%$ inhibiton vs. vehicle control, n=3, $p<0.001$). These data were also confirmed using the PKC inhibitor H7 (Nakadate, T., et al. (1989). *Mol. Pharmacol.* 36: 917-924.) (100 µM final concentration, $91 \pm 4\%$ inhibition compared to vehicle control, n=3, $p<0.001$). Likewise, the LXA$_4$-elicited (10 nM) increment in migration was sensitve to staurosporine ($89 \pm 7\%$ inhibition compared to vehicle control, n=3, $p<0.001$). Pre-exposure of PMN to pertussis toxin, Nigam, S., et al. (1990).

*J. Cell Physiol* 143: 512-523), (2 µg/ml) also inhibited baseline fMLP driven migration (91±8% inhibition compared to vehicle control, n=6, p<0.001). The LXA$_4$-elicited (10 µM) increase in PMN migration (46±3% increase compared to control, p<0.01) was also sensitive to PMN pre-exposure to pertussis toxin (87±4% inhibition of control, n=6, p<0.001).

Next assessed was the possibility of differential sensitivity to staurosporine for baseline and LXA$_4$-stimulated increases in fMLP-driven PMN migration. Staurosporine inhibited baseline PMN transepithelial migration in a dose dependent manner (94±4%, 96±9%, 67±11%, 54±8%, 35±11% and 11±6% inhibition compared to vehicle controls for concentrations of 100, 10, 1, 0.1, 0.01 and 0.001 nM staurosporine, respectively, p<0.01 by ANOVA). From this dose response, a concentration was selected which was approximately half-maximal in inhibiting PMN migration (0.11 nM, see above). PMN were then preexposed to staurosporine (0.11 nM, 15 min, 37° C.), washed free of inhibitor, and subsequently assessed for the LXA$_4$ effect on PMN transepithelial migration. Here, the LXA$_4$-elicited increase in transepithelial migration of PMN was observed to be sensitive to PKC inhibition, since the relative inhibition by staurosporine was equivalent with and without LXA$_4$ (54±6% and 49±7% decrease in total PMN migration for staurosporine treated PMN in the presence and absence of LXA$_4$, respectively, p=n.s.; both decreased compared staurosporine untreated controls, n=6, p<0.025).

These results indicate that LXA$_4$-elicited increases in PMN migration in the apical-to-basolateral direction are not sensitive to inhibition of the cyclooxygenase pathway or the specific inhibition leukotriene generation, but is sensitive to inhibitors of PKC.

Discussion:

During inflammatory processes, PMN are recruited from the blood by signals derived at inflammatory sites. At sites of acute inflammation, PMN function may be regulated by a variety of inflammatory signals, including both protein- and lipid-derived signals. PMN function at organ-specific sites, including the intestine, are thought to contribute to epithelial dysfunction during disease. Here it is reported for the first time that the arachidonic acid-derived eicosanoid, LXA$_4$, modulates PMN migration across a model human intestinal epithelium. In addition, it is here reported that LXA$_4$ exerts an effect on migration in a polarized fashion.

LXA$_4$ enhances PMN transepithelial migration in the apical-to-basolateral direction. For technical reasons, previous studies of PMN transepithelial migration have focused on "non-physiologically" oriented monolayers, in which leukocyte migration is in the apical-to-basolateral direction, (Nash S., et al. (1987). *J. Clin. Invest.* 80: 1104-1113), (Migliorisi G. E., et al. (1988). *J. Leukocyte Biol.* 44:485-492), (Parkos C. A., et al. (1991). *J. Clin. Invest* 88:1605-1612), (Evans C. W., et al. (1983) *Br. J. Exp. Pathol.* 64: 644-654). PMN pre-exposed to LXA$_4$ and driven to trnigrate across epithelial monolayers oriented non-physiologically resulted in enhanced PMN migration.

The action of LXA$_4$ was found to be specific for PMN, and not epithelial cells, since enhanced PMN migration in this direction was dose- and time-dependent, and no measureable effects on PMN transepithelial migration were observed when epithelial monolayers were pre-exposed to LXA$_4$ under conditions which promoted enhanced PMN migration. These results are consistent with previous studies which report that LXA$_4$, in similar concentrations used here, was capable of activating PMN in vitro. In this model system, LXA$_4$ enhanced PMN migration in a manner independent to that of FMLP, since in all conditions PMN migration was driven toward a gradient of fMLP, suggesting that the proportion of PMN migration exceeding that of fMLP controls is dependent on a LXA$_4$-mediated event. Moreover, these results suggest that the action of LXA$_4$ may be synergistic with fMLP, since LXA$_4$, by itself, does not promote PMN migration in the absence of fMLP.

In addition, it was discovered that pre-exposure of PMN to LXA$_4$ modulates migration of PMN in a polarized manner. That is, opposite effects were observed depending on the direction of PMN migration. The observed effect of LXA$_4$ inhibition of PMN migration in the physiologically oriented (basolateral-to-apical) direction was dependent on concentration— as well as the duration of pre-exposure. These effects were found to be selective for LXA$_4$, since no effect was observed with the positional isomer LXB$_4$.

As described for leukocyte movement across endothelia, (Butcher E. C. (1991) *Cell* 67: 1033-1036), PMN migration across epithelial monolayers is likely a multi-step process requiring engagement and disengagement of several receptor-ligand complexes between PMN and epithelial cell. The specific events involved in PMN transepithelial migration are poorly understood at the present time, but in part requires the PMN B2 integrin CD11b/CD18 and is independent of ICAM-1. (Parkos C. A., et al. (1991). *J. Clin. Invest* 88: 1605-1612). In addition, PMN transepithelial migration can be regulated by exposure of T84 epithelial monolayers to the lymphokine interferon-gamma (IFN-γ). In light of the polarized nature of this epithelium, (Madara, J. L., and K. Dharmsathaphom (1985). *J. Cell Biol.* 101: 2124-2133), (Madara J. L., et al. (1987). *Gastroenterology* 92: 1133-1145), (Dharmsathaphom K., and J. L. Madara (1990). *Meth. Enzymol.* 192: 354-389), it would not be surprising that the sequence by which PMN encounters epithelial ligands directly regulates PMN migration.

Moreover, PMN migration across endothelia requires a sequential series of activation and deactivation steps on the PMN surface, of which lipid-derived activating factors may play an important role (reviewed in Butcher E. C. (1991) *Cell* 67:1033-1036). Whether LXA$_4$ could act as a lipid-derived factor for expression of a crucial ligand in the regulation of PMN migration across epithelia is not known. Evidence to support this hypothesis are provided by a recent study characterizing lipoxin binding sites on human PMN. (Palmblad J., et al. (1987) *Biochem. Biophys. Res. Commun.* 145: 168-175). With a reported K$_d$ of 0.5 nM and approximately 1800 binding sites/cell, the range of LXA$_4$ concentrations used in the present study (0.01-10 nM) should provide maximal activation of subsequent signal transduction steps, most of which remain to be elucidated, but appears to involve a G-protein associated activation step (Fiore S., et al. (1992) *J. Biol. Chem.* 267: 16168-16176), and possibly a signalling step through PKC as determined by inhibition using staurosporine.

Recent in vivo studies have shown that LXA$_4$ is an important lipid-derived mediator at several distinct anatomic sites, including the lung, (Christie P. E., et al. (1992) *Am. Rev. Respir. Dis.* 145: 1281-1284), kidney, (Katoh T., et al. (1992) *Am. J. Physiol.* 263: F436-F442), blood vessel (Brezinski D. A., et al. (1992) *Circulation.* 86: 56-63), and hamster cheek pouch (Hedqvist P., J. et al. (1989). *Acta. Physiol. Scand.* 137: 571-572). The data reported here suggest that LXA$_4$-elicited alterations exert effects at the level of PMN and subsequently modulate PMN-epithelial interactions. Previous studies have shown that production of lipoxygenase products of arachidonic acid correlate with intestinal inflammation. Specifically, an enhanced conversion of arachidonate to 5-, 12- and 15-hydroxy-eicosatetraenoic acid (HETE) has been shown in ulcerative colitis homogenates (Broughton-Smith, N. K., et al. (1983) *Gut* 24: 1176-1182), as well as increased biosynthesis of $LTB_4$ in Crohn's disease (Sharon, P. and W. F. Stenson (1984) *Gastroenterology* 86: 453460). The present results demonstrate that lipoxins, and especially by their action on PMN, play a role in intestinal disease.

EXAMPLE 2

Measurement of Electrical Parameters of Cultured Epithelial Monolayers: Use in Assessing Neutrphil-Epithelial Interactions Materials and Methods General information regarding T84 cells: T84 cells were negative for mycoplasma as tested commercially using a nucleic acid probe (Organon TeKnika Corp., Rockville, Md.). T84 cells were first obtained from Dharmsathaphorn in 1984 (Dharmsathaphorn, K. *Am. J. Physiol.* 246 (Gastrointest. Liver Physiol. 9):G204-G208; 1984). T84 cells were originally isolated from a lung metastasis of a patient with colonic carcinoma and were established as a transplantable line in BALB/c nude mice (Dharmsathaphorn, K. *Am. J. Physiol.* 246 (Gastrointest. Liver Physiol. 9):G204-G208; 1984). However, T84 cells are now available from the ATCC (American Type Culture Collection, Rockville Md, cat #CCL 248). ATCC derived T84 cells passages 60-100 have been compared with the original distributed parent line (passages 16-40) by assaying electrogenic Cl⁻ secretory responses to cAMP (8-bromo-cAMP, theophylline, or forskolin) and $Ca^{+2}$ (ionomycin, A23187, carbachol) agonists, cell migration patterns, neutrophil transmigration, and cytoskeletal responses to bacterial (*C. difficile* toxin A) and fungal (cytochalasin D) derived toxins. The cells from these two sources are highly comparable. Some differences between T84 cells from these two sources do exist in conditions for loading cells with reagents which cross the plasma membrane passively (such as loading phalloidin into living cells (Shapiro, M. et al; *J. Clin. Invest.* 87:1905-1909; 1991)). However, even within cells from ATCC, optimal loading conditions can vary substantially over 20-25 passages and thus loading conditions with cells from any source must be empirically defined in each laboratory.

Growth and Maintenance of T84 cells: As previously detailed (Dharmsathaphorn, K.; Madara, J. L. *Meth. Enzymol.* 192:354-389; 1990), T84 cells are grown as monolayers in a 1:1 mixture of Dulbecco-Vogt modified Eagle's (DME) medium and Ham's F-12 medium supplemented with 15 mM $Na^+$-HEPES buffer, pH 7.5, 1.2 µl $NaHCO_3$, 40 mg/liter penicillin, 8 mg/liter ampicillin, 90 mg/liter streptomycin, and 5% newborn calf serum. Growth requirements are not strict as cells will grow in a variety of media (Dharmsathaphorn and Madara, personal observations, (Dharmsathaphorn, K.; Madara, J. L. *Meth. Enzymol.* 192:354-389; 1990). However, some care must be taken in selecting media, since media selected strictly for the ability to increase growth rate can result in the loss of the polarized phenotype (Madara, personal observations). Cells are split near confluency by incubating in 0.1% trypsin and 0.9 mM EDTA in Ca+2 and Mg+2 free phosphate buffered saline for 15-20 min. T84 cells grow best when split 1:2 and plating at lower densities may greatly retard growth. After splitting, cells are generally near confluency once again in 5-8 days; thus they are relatively slow growing cells. T84 cells aggregate in suspension and attempts to produce uniform dispersal of cells will result in substantial loss of viability and resulting low effective plating density.

Preparation of monolayers: Normal or inverted monolayers can be constructed for a physiological microassay using the commercially available insert system (Costar inserts, 0.33 cm², 5 µm polycarbonate filters). The larger pore size is crucial for allowing neutrophils to penetrate the filter. Collagen 1 must coat the filters to allow attachment of T84 cells. Original descriptions of the collagen coat involved procedures in which the collagen was chemically crosslinked Dharmsathaphorn, K. et al; *Meth. Enzymol.* 192:354-389; 1990. Dharmsathaphorn, K. et al; *Am. J. Physiol.* 246 (Gastrointest. Liver Physiol. 9):G204-G208; 1984. However, neutrophil movement across crosslinked collagen gels has been found to be extremely limited.

To circumvent this problem, Cereijido and Sabatini's method (Cereijido, M.; Sabatini, D. D. 1978 *J. Cell Biol.* 77:853-876;) of preparing viscous collagen from rat tail tendons is followed and this solution is mixed 1:3 with 60% ethanol at 4° C. Very little collagen is required; indeed collagen ethanol ratios of 1:100 can be readily used. Fifty microliters of this mixture is then placed on each filter, taking care of an even distribution and plates are allowed to dry in a hood (3 hr—overnight). A few drops of media are then added to the wells for 1-3 hr, and cells ($10^6/cm^2$) are then added in a total volume of 167 µl. Eight-hundred microliters of media are added to the outer wells and a few drops of additional fresh media to the inner well.

After reaching the initial steady state resistance, the monolayers should be used within 6-14 days for two reasons: first, physiological responses such as Cl⁻ secretion will diminish with time and second, without underlying crosslinked collagen, cell processes can eventually move through the 5 µM pores and ultimately result in a near double monolayer (monolayer on each side of the filter). Monolayers need only have one feeding, but this should take place at least 24 hrs prior to experimental use.

Inverted monolayers can also be grown using this technique. For this 0.8 mm thick lexan rings having the same dimension of the base of Costar inserts are machined, deburred, cleaned by boiling with a trace of detergent and subsequently exhaustively washed, and attached to the underside of the insert using General Electric RTV Silicone glue (this underside ring is necessary for a peripheral electrical seal). After drying overnight, the inserts are sterilized by submersion in 70% ethanol (4-hr overnight), inverted onto a sterile petri dish in a hood, and allowed to dry. Collagen and cells are added to the filter (underside now facing up) exactly as with unmodified inserts and cells are allowed to attach for 4 hours before righting the inserts into the 24 well holding plates. Subsequent treatment of the monolayers is identical to that described above.

Isolation of neutrophils: Neutrophils are isolated from whole blood using a gelatin-sedimentation technique. Briefly, whole blood, anticoagulated with citrate/dextrose, is centrifuged at 300×g for 20 minutes (20° C.). The plasma and buffy coat are carefully removed using a curved, siliconized glass pipette which is attached to a vacuum trap. Care must be taken not to aspirate the interface between the buffy coat and RBC since this is where PMN reside. To eliminate contaminating RBC, a 2% solution of gelatin (100 bloom, Fisher) made up in either saline or HBSS (3540° C.) is added to the RBC/PMN mixture at a ratio of 35 ml of gelatin per 15-20 ml of cells.

The gelatin/cell mixture is then incubated at 37° C. for 30 minutes to settle-out contaminating RBC. The pink supernatant is then centriged at 400×g for 10 minutes (20° C.) to yield a red pellet of PMN and some RBC's. Residual RBC's are then lysed by gentle resuspension of the pellet with isotonic ammonium chloride (t=4° C.), followed immediately by centrifugation at 300×g, 10 minutes, 4° C. After washing twice in HBSS (HBSS without $Ca^{+2}$ or $Mg^{+2}$), the cells can be counted and resuspended at $5 \times 10^7$ PMN/ml and are ready for use. The above method usually yields $1-2 \times 10^8$ PMN from 100 ml of whole human blood at a purity of approximately 90%.

Physiological assays: All solutions and materials are maintained at 37° C. A convenient way to do this is to perform the experiments in a 37° C. room. T84 cells do well in this environment in bicarbonate free buffers for at least four hours. Hanks Balanced Salt Solution (HBSS, Sigma, without bicarbonate or phenol red) to which 10 mM HEPES buffer is added, pH 7.4 is used for these assays. Inserts with attached monolayers are lifted from wells, drained of media by inverting, and gently rinsed by dipping in a 200 ml container of HBSS. Inserts are then placed in new wells with 800 µl fMLP in the lower compartment and subsequently 100 µl HBSS is added to the inner well (an additional 100 µl containing neutrophils in HBSS is added to the inner well to initiate the experiment). The above treatment has little effect on resistance but washing or other trauma does consistently result in a transient transepithelial current (4-15 $uA/cm^2$) which returns to baseline (0-3 $\mu A/cm^2$) within 4 minutes.

To measure currents, transepithelial potentials, and resistance, the following system was utilized: a commercial voltage clamp (Iowa Dual Voltage Clamps, Bioengineering, University of Iowa), interfaced with an equilibrated pair of calomel electrodes submerged in saturated KCl and with a pair of Ag—AgCl electrodes submerged in HBSS. Agar bridges are then made: HBSS containing 6% agar is heated in a water bath until the agar is in solution and the solution is perfectly clear. Using a syringe for suction, this hot solution is then pulled through 1 mm bore polyethylene tubing (12 cm lengths), the agar is allowed to gel, and the ends are trimmed to a 45 tapper with a razor blade. Agar bridges are then used to interface the electrodes with the solutions on either side of the monolayers-(one calomel and one Ag—AgCl electrode in each well).

The agar bridge pair to the inner well is properly positioned when the surface tension of the fluid above the monolayer is broken. The pair of bridges in the outer well is positioned by inserting the agar bridges to the bottom of the well (through one of the openings on the side of the insert) and then withdrawing it 1 mm. In practice, a hand-held polycarbonate strip, which fixes all distances and positions, had been made. Such a bridge-holding device makes use of the fact that all distances are fixed (from top of well to monolayer, from side of well to insert center, etc.). In high resistance monolayers, such as T84, positional effects are minimal. This is likely due to the relatively high resistance of the monolayer which promotes relatively uniform current densities at the monolayer surface. The taper in the tips of the agar bridges is also advantageous in preventing entrapment of air bubbles when gently positioning the inner bridges and in preventing abutment of the outer bridges with the plate bottom which leads to spuriously high resistance readings.

For measurements, bridges are positioned as described, and the spontaneous transepithelial electrical potential and the instantaneous potential generated by passing 25 µA of current are measured. Similar measurements are taken after scraping the filter with a pipette and these later measurements are used to correct for system resistance. Using these values and Ohm's Law, tissue resistance and transepithelial current are then calculated. System resistance is less than 5% of the total resistance value. In a single monolayer in which the bridges were simply held by hand and repositioned 20 times (making sure that both electrode pairs were varying in position) resistance and spontaneous transepithelial electrical potential varied by less than 10%. In setting up inverted monolayers for study one must be cautious that small air bubbles are not trapped under the monolayer by the added ring. This problem can be circumvented by lowering the washed insert into the HBSS of the outer well slowly and at an angle.

In practice the above approach allows one to serially record plates of monolayers and accurate readings from 36 monolayers can be obtained in less than 10 minutes.

Myeloperoxidase assay of neutrophil transepithelial migration: PMN contents of monolayers and lower chambers can be quantitated by assaying the PMN-specific azurophil granule marker, myeloperoxidase (MPO). Monolayers are cooled to 4° C. and washed with HBSS using a pipette to remove non-adherent PMN. Washed monolayers are then placed in new 24-well tissue plates and overlaid with 1.0 ml 0.5% Triton X-100 in HBSS in order to solubilize PMN-associated MPO. After 10 minutes of vigorous shaking, monolayers can then be discarded and supernatant saved for assay. To the original lower chambers, MPO can be solubilized by simply adding 50 µl of 10% Triton X-100 and mixing.

To assay for solubilized MPO, the pH of solubilized chambers and monolayers must be adjusted to 4.2 using 100 µl of 1.0 M citrate pH 4.2. Aliquots of each pH adjusted sample can then be transferred to a 96-well microtiter plate for substrate addition. After adding 100 µl of a solution of 2 mM 2,2-azino-di-(3-ethyl) dithiazoline sulfonic acid (ABTS), 0.06% $H_2O_2$ in 100 mM citrate buffer pH 4.2 to each well, color development can be quantitated on a microtiter plate reader at 405 nm. The reaction can be terminated by the addition of sodium dodecyl sulfate to a final concentration of 0.5%. For standards, serial dilutions of the same PMN used in the experiment can be made in 1.0 ml of HBSS. MPO is solubilized identically as for the lower chambers. When performed in this manner, the assay is linear in the range of $0.3-50 \times 10^4$ cells/ml.

Results

Steady state resistance was reached within 7 days of plating and values greater than 1,000 ohm $cm^2$ were achieved. Both the time course and value of resistance are comparable to that achieved on matrices of cross-linked collagen (Omann, G. M. et al.; *Physiol. Rev.* 67:285-322; 1991). Passage-related variation in time to reach physiologic confluence (4-7 days) and in resistance value in the steady state (500-1900 ohm $cm^2$) does occur. Resistance is measured by the simple bridge method described. The time course and steady state resistance value achieved is comparable to that previously published for monolayers on thick cross-linked collagen I matrices measured by formal Ussing chamber means (Madara, J. L; Dharmsathaphorn, K. *J. Cell Biol.* 101:2124-2133; 1987). The collagen matrix does not inhibit epithelial transmigration by neutrophils and thus is suitable for such assays. The approach to measurement of resistance allows one to obtain sequential values from numerous monolayers over a short duration of time.

Neutrophil migration across T84 monolayers was accompanied by a significant decrease in transepithelial resistance when migration was in the apical to basolateral direction. The size of the resistance decrease was paralleled by the density of applied neutrophils. Neutrophil densities in cell number/$cm^2$ are indicated. Transmigration (apical to basolateral) was stimulated by a $10^{-7}$ M transepithelial gradient of fMLP. The decrease in resistance due to penetration of intracellular tight junctions by neutrophils was large at the highest neutrophil density and is saturated within 60 minutes. Furthermore, as indicated by the myeloperoxidase assay, the log of resistance correlates well with the number of neutrophils migrating into the membrane (cells having crossed the tight junction but remaining above the filter) and with the total number of transmigrated cells. The log of the final resistance value ($5 \times 10^6$ neutrophils/cm$^2$ in $10^{-7}$ M fMLP gradient for 110 min) correlates with the number of neutrophils transmigrated. Variations in electrical responses are due to variations in efficacy of transmigration.

The decrease in resistance was only modest in the absence of a gradient and under these conditions the number of transmigrating neutrophils was small. Antibody to the common beta chain of neutrophil $\beta_2$ integrins (CD18) blocks transmigration and the fall in resistance while a control antibody (J5) recognizing CD10 has no inhibitory effect. The fall in resistance seen in controls (no fMLP, no PMN) and in the presence of anti-CD18 antibody represents, in large part, the 200-300 ohm fall in resistance occurs when monolayers are transferred from media to HBSS.

fMLP was effective in stimulating transmigration of neutrophils at both $10^{-6}$ and $10^{-7}$ M as measured by either resistance or myeloperoxidase assay.

TABLE 1

NEUTROPHILS MIGRATE ACROSS INVERTED, SPARSELY COLLAGEN-COATED INSERTS AND SUBSEQUENTLY ACROSS T84 MONOLAYERS (i.e. BASOLATERAL TO APICAL)

| | Neutrophil Cell Equivalents × 10$^{4*}$ | | |
|---|---|---|---|
| | In Monolayers | In Opposite Reservoir | Total |
| No FMLP$^+$ | 0.23 | 0.18 | 0.41 |
| No PMN | 0 | 0 | 0 |
| FMLP + PMN | 5.47 | 85.30$^\#$ | 90.77$^\#$ |
| FMLP + PMN + αCD18 | 1.22 | 5.76 | 7.00 |

*Values represent means of three determinations;
$^+$FMLP = $10^{-6}$ M; PMN = $6 \times 10^6$/cm$^2$;
$^\#$FMLP + PMN are significantly different (P < .0001) from all other groups.

Additionally, the blocking antibody to CD18 inhibited neutrophil transmigration nearly completely as assessed by each assay, while substantial transmigration proceeded in the presence of control antibody (anti-CD10). Transmigration which is inhibitable by antibody to CD18 also occurred in the basolateral to apical direction (Table 1). Neutrophils applied to the basolateral surface of monolayers have effects on resistance independent of transmigration and thus the myeloperoxidase assay is most useful in this direction as a quantitative measure of transmigration.

As previously reported in Nash, S. et al; *J. Clin. Invest.* 87:1474-1477; 1991, a neutrophil derived secretagogue (NDS) activity, detected as a modest short circuit current, occurs as a consequence of neutrophil-T84 cell interactions. Such currents are readily detected in the microassay described, are important since they represent active electrogenic transepithelial transport events, and are not readily detected using "chop-stick" type detection systems.

Discussion

Detailed here are useful approaches in utilizing T84 cells for studies of epithelial monolayer function in general and epithelial-neutrophil interactions in particular. Electrical data obtained from Ussing chambers designed for cultured monolayers (Dharmsathaphorn, K.; Madara, J. L., *Meth, Enzymol.* 192:354-389; 1990. Nash, S. et al; *J. Clin. Invest.* 87:1474-1477; 1991. Dharmsathaphom, K. et al; *Am. J. Physiol.* 246 (Gastrointest. Liver Physiol. 9):G204-G208; 1984) are highly accurate. However, in using such systems one is limited by the number of such chambers available, each of which is occupied by one monolayer for the length of the experiment. Additionally, such systems have traditionally been designed to accommodate monolayers with large surface areas (such as 2 cm$^2$) since larger surface areas provide for more accurate transepithelial flux measurements. However, flux measurements are often only required to address specific issues and the bulk of many experiments can often be completed with simple electrical assays of resistance and short circuit current.

Electrical data with reproducibility rivaling that of more formalized but tedious systems can be obtained, in high resistance epithelial monolayers such as T84, by simply interfacing electrical measuring systems usually utilized in more formal Ussing chamber systems, with a commercially available insert system. It would not be surprising if the electrical data derived from this system were of less quality in low resistance monolayers, since imposed current densities at the monolayer surface would likely be less uniform and therefore positional effects could be more problematic. Moreover, it is not likely that the insert system will be suitable for non-electrical assays of permeability such as flux. Major limitations in this regard are the lack of stirring and the overly small compartment (apical) from which to obtain samples.

Also described is a simple procedure for manufacturing inverted monolayers so that neutrophils or other cells can settle by gravity on the basolateral side of the monolayer. In this system, attention to composition of the matrix on which one plates cells determine whether cells and macromolecules added to the basolateral surface are able to gain access to the basolateral membrane of the epithelial cell. Lastly, a simple enzymatic assay which allows quantitation of numbers of neutrophils which have migrated either into or across epithelial monolayers is described.

The data presented, which show examples of the application of these approaches to types of studies previously assessed in formalized Ussing chamber experiments, indicate that such methods are useful for detecting the physiologic effects of neutrophil-epithelial interactions on epithelial barrier function and activated transepithelial electrogenic transport. The approach outlined can be used to show that intestinal epithelial barrier function is diminished and Cl$^-$ secretion is activated by such neutrophil-epithelial interactions. Both of these functional disorders of intestinal epithelia are known to occur in vivo in humans affected by intestinal diseases characterized by neutrophil infiltration of the epithelium. Thus, such in vitro cell culture models of the interactions between these two cell types provide an opportunity for mechanistic studies of the symptomatology occurring in these important human diseases,

EXAMPLE 3

Synthesis of Lipoxin Analog Compounds

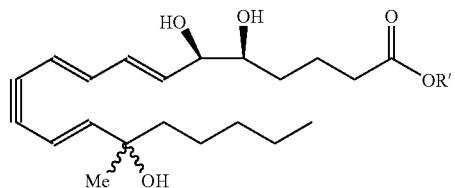

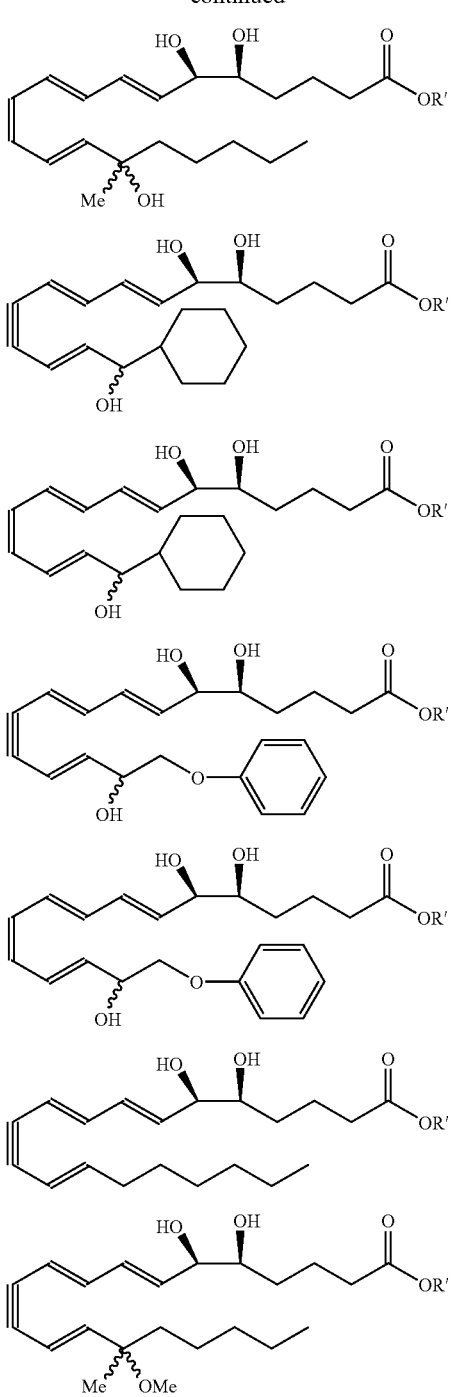

Preparation of the Methyl Ester Precursor of Compound 1:

To a solution of 3-methyl-3-trimethylsiloxy-1-bromo-1-octene (130 mg. 0.44 mmol) in benzene (1.5 mL) was added n-propylamine (0.05 mL, 0.61 mmol) and Pd(PPh$_3$)$_4$ (20 mg. 0.02 mmol) and the solution was protected from light. It was then degassed by the freeze-thaw method and stirred at rt for 45 min. (7E, 9E, 5S, 6R) Methyl 5,6-di(tert-butyldimethylsiloxy)-dodeca-7,9-diene-11-ynoate (183 mg. 0.44 mmol) (compound 12) and copper iodide (14 mg. 0.07 mmol) were added and the solution was one more time degassed by the freeze-thaw method. The mixture was stirrred for 3 h at rt and quenched with saturated aqueous solution of NH$_4$Cl and extracted with ether. It was then washed with brine and dried over MgSO$_4$ and the solvent was evaporated. Flash column chromatography (silica, 3% ether hexanes) afforded pure compound as a colorless liquid (171 mg. 57% yield).

To a solution of the compound (171 mg. 0.25 mmol) in THF (0.5 mL) was added n-BuN$_4$F (0.9 mL. 0.90 mmol) and the mixture was stirred at rt. The reaction was completed in 2 h at which time it was poured into water and extracted with ether. The ether extracts were washed with brine, dried over Na$_2$SO$_4$ and the solvent was evaporated. Flash column chromatography (silica 4% MeOH/CH$_2$Cl$_2$) afforded the methyl ester (24 mg.) together with some of the corresponding lactone. HPLC retention time: 9:39 min (microsorb reverse phase, 4,6 mm×25 cm, C-18 column, MeOH/H$_2$O 70:30 flow rate 1 ml/min, UV detector at 300 nm). UV in MeOH: $\lambda_{max}$283, 294, 311 nm. $^1$H NMR (500 MHz CDCl$_3$) δ6.53 (dd. 15.210.9 Hz, 1 H), 6.32 (dd, J=15.1, 11.0 Hz, 1 H), 6.17 (d, J=15.9 Hz, 1 H) 5.83 (dd. J=17.5, 2.1 Hz, 1H), 5.80 (dd. J=15.2, 6.7 Hz, 1 H), 5.72 (dd. J=17.0, 2.1 Hz, 1 H), 4.14 (m, 1 H), 3.68-3.64 (m, 4H), 2.35-2.31 (m, 2 H), 1.51-1.48 (m, 1 H), 1.43-1.42 (m, 2 H), 1.30-1.23 (m, 15 H) 0.85 (t, 3 H). $^{13}$C NMR (126 MHz, CDCl$_3$) δ 150.01, 140.18, 132.95, 132.26, 112.43, 107.50, 75.23, 73.76, 42.49, 33.67, 32.17, 31.36, 27.96, 23.56, 22.58, 21.03, 14.03.

Preparation of the Methyl Ester Precursor of Compound 2:

A solution of the methyl ester precursor of compound 1 (3 mg. in CH$_2$Cl$_2$ (1 ml) was mixed with Lindlar's catalyst (1 mg.) and placed under a hydrogen atmosphere. The mixture was stirred at rt in the dark followed by HPLC until about 80% conversion (1 h). Filtration over celite evaporation of the solvent and separation by HPLC gave a pure methyl ester. HPLC retention time: 10:02 min (microsorb reverse phase. 10 mm×25 cm C-18 column, MeOH/H$_2$O 70:30 flow rate 4 ml/min. UV detector at 300 nm). UV in MeOH: $\rho_{max}$ 287, 301, 315 nm.

Preparation of the Methyl Ester Precursor of Compound 3:

This compound was prepared similarly to the preparation of the methyl ester precursor of compound 1 (from 3-cyclohexyl-3-trimethylsiloxy-1-bromo-1-octene). Desilylation of this compound was also performed in a similar manner to afford the methyl ester. HPLC retention time 8:02 min (microsorb reverse phase, 4.6 mm×25 cm. C-18 column, MeOH/H$_2$O 70:30, flow rate 1 ml/min, UV detector at 300 nm). UV in MeOH: $\lambda_{max}$ 282,293, 311 nm. $^1$H NMR (360 MHz, CDCl$_3$) δ 6.56 (dd, 15.4, 10.9 Hz, 1 H), 6.33 (dd, J=15.2, 10.9 Hz, 1 H), 6.13 (dd, J=15.8, 6.5 Hz, 1 H), 5.81 (dd, J=15.2, 6.4 Hz, 1 H), 5.80 (d, J=15.6 Hz, 1 H), 5.73 (dd, J=15.4, 2.1 Hz, 1 H), 4.15 (br, 1H), 3.93-3.90 (m, 1 H), 3.67 (br, 1H), 3.65 (s, 3H), 2.34 (t, 2H), 1.82-1.65 (m, 10 H), 1.46-1.38 (m, 3H), 1.26-1.01 (m, 5H).

Preparation of the Methyl Ester Precursor of Compound 4:

Selective hydrogenation of the methyl ester precursor of compound 3, followed by HPLC purification gave the methyl ester precursor of compound 4. HPLC retention time: 9.72 min (microsorb reverse phase, 10 mm×25 cm C-18 column, MeOH/H$_2$O 70:30 flow rate 4 ml./min. LV detector at 300 nm), LV in MeOH: $\lambda_{max}$ 288, 301, 315 nm. $^1$H NMR (250 MHz, C$_6$D$_6$) δ 6.66-6.89 (m, 2 H), 5.95-6.24 (m, 4H), 5.55-5.66 (m, 2 H), 3.82 (m, 1 H), 3.73 (m, 1 H), 3.41 (m, 1 H), 3.31 (s, 3H, OCH$_3$), 2.08 (t, 2H, CH$_2$COO), 1.00-1.81 (m, 18 H).

The methylesters can be converted to corresponding alcohols using standard techniques.

Synthesis of 15(R)-15-methyl-LXA$_4$ and 15(±)methyl-LXA$_4$

Approximately 1 gm acetylenic ketone a is prepared using Friedel-Crafts acylation of bis(trimethylsilyl)acetylene with hexanoyl chloride and is reduced using (−)-pinayl-9-BBN to give the (S) alcohol in CH$_3$N$_2$ as in Webber, S. E. et al. (1988)

Adv. Exp. Med. Biol. 229:61; Nicolaou, K. C. et al. (1991) Angew. Chem. Int. Ed. Engl. 30:1100; and Vorbrüggen, H. et al.: In: Chemistry, Biochemistry, and Pharmacological Activity of Prostanoids (Roberts, S. M., Scheinmann, F. eds.). Oxford: Pergamon Press, to generate the methyl at C-15.

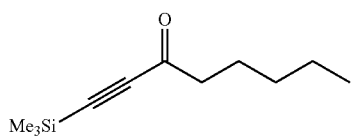

a

Alternatively, the keto group can be treated with CH₃MgBr (60=>70° C.) as in Vorbrüggen, H. et al.: In: Chemistry, Biochemistry, and Pharmacological Activity of Prostanoids (Roberts, S. M., Scheinmann, F. eds.). Oxford: Pergamon Press to yield the 15(±)methyl of b (2-5 g) in dry CH₂Cl₂ (~20 ml) at 0° C. with sequential additions of 2,6-lutidine (5.2 ml) and tert-butyldimethylsilyl triflate (6.9 ml). This reaction is mixed for 1 h and then diluted with 100 ml ether for aqueous extraction and drying with MgSO₄.

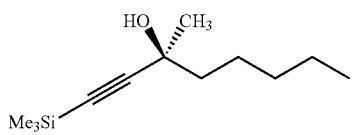

b

The product c is then coupled with d

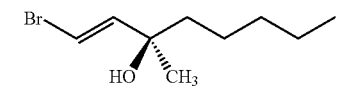

c

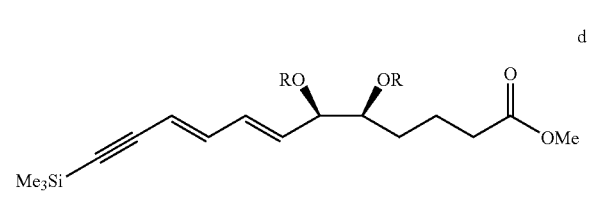

d that is generated as in Nicolaou, K. C. et al. (1991) *Angew Chem. Int. Ed. Engl.* 30:1100; Nicolaou, K. C. et al. (1989) *J. Org. Chem.* 54:5527 and Webber, S. E. et al. (1988) *Adv. Exp. Med. Biol.* 229:61. Structure d from fragment A in Scheme I is suspended in 4.0 equiv. of AgNO₃, then 7.0 equiv. of KCN, containing EtOH:THF:H₂O (1:1:1), 0-25° C. for 2 h to generate the C-methyl ester protected 15-methyl-LXA₄ analog that is concentrated and saponified in THF with LiOH (2 drops, 0.1 M) at 4° C. 12-24 h to give the corresponding free acid.

Synthesis of 16-dimethyl-LXA₄

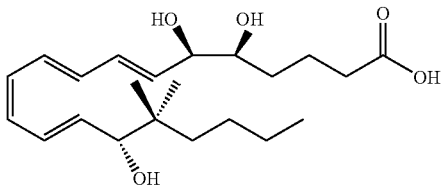

This compound is generated using the similar strategy by coupling d above with e vide supra, or f to generate the 15-phenyl-LXA₄ analog, or g to generate the 17-m-chlorophenoxy-LXA₄ analogs.

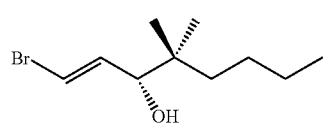

e

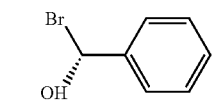

f

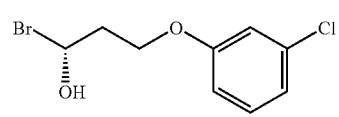

g

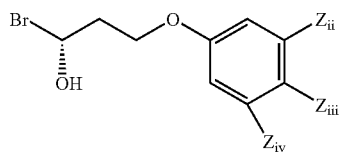

h

The appropriate C fragments in Scheme I (i.e. e, f, g, h,) are each prepared as reviewed in Radüchel, B. and Vorbrüggen, H. (1985) Adv. Prostaglandin Thromboxane Leukotriene Res. 14:263 for the known corresponding prostaglandin analogues. In h, R═H; Cl, methoxy or halogen.

Synthesis of 13,14-Acetylenic-LXA₄ and Haloen-Containing Analogs.

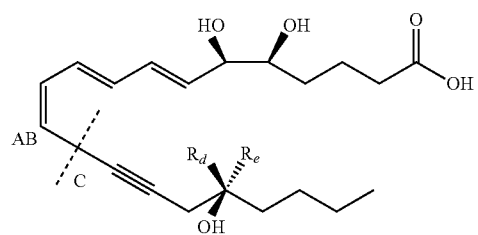

Using the A₂B₂ generated fragment from Scheme II, the corresponding C2 fragments are prepared for coupling. Structures j and k are generated as in Nicolaou, K. C. et al. (1989) J. Org. Chem. 54:5527 and methylated as in Radüchel, B. and Vorbrüggen, H. (1985) Adv. Prostaglandin Thromboxane Leukotriene Res. 14:263 are coupled to 7 to yield these LX analogues. The materials may be subject to RP-HPLC for purification vide supra.

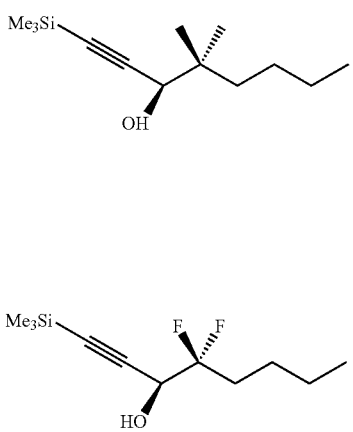

Synthesis of 14,15-Acetylenic-LXA₄.

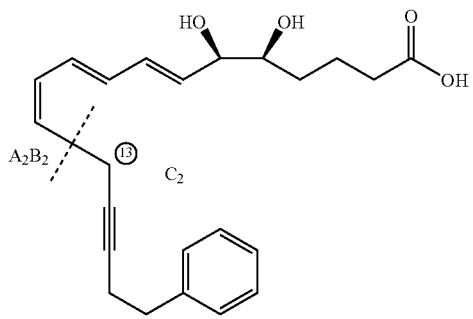

The designated combined A₂B₂ fragment can be prepared from couplings of fragments A₁ and B₁, illustrated in Route II to carry the structure of 7 or 4 vide supra for coupling to fragment C₂. The precursor for the C₂ fragment 1 can be prepared as in Radüichel, B. and Vorbrüiggen, H. (1985) Adv. Prostaglandin Thromboxane Leukotriene Res. 14:263 for a prostaglandin analog.

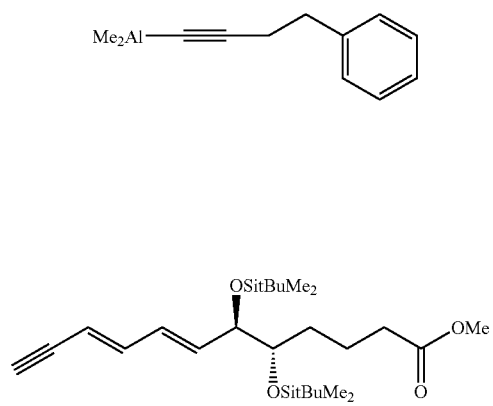

Precursor m as prepared previously (Nicolaou, K. C. (1989) J. Org. Chem. 54:5527) is added at 1.2 equiv. to 0.05 equiv. of Pd(PPh₃)₄, 0.16 equiv. of CuI, n-PrNH2, in benzene with Me2Al-carrying L 1, 2-3 h RT to yield n.

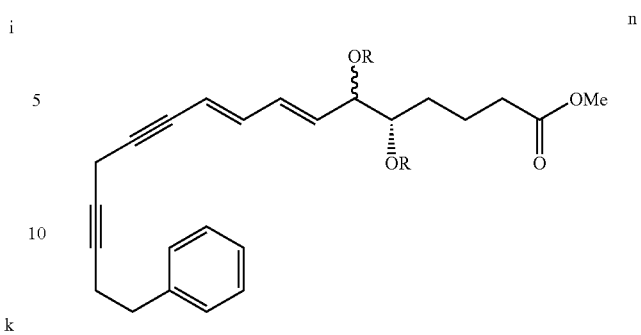

The alcohol protecting groups TBDMS=R are removed with 10 equiv. of HF-pyr, THF, 0-25° C. (4 h) followed by exposure to ~3.0 equivalents of Et₃N, MeOH, 25° C. 15 min to open acid-induced δ-lactones that usually form between C-1-carboxy and C—5 alcohol in the lipoxins (Serhan, C. N. (1990) Meth. Enzymol.187:167 and Nicolaou, K. C. (1989) J. Org. Chem. 54:5527). After mild treatment with Lindlar cat. 5% by weight, the extracted material may be subjected to LiOH saponification in THF to generate the free acid of the target molecule that can be subject to further purification by RP-HPLC gradient mobile phase as in (Serhan, C. N. et al. (1990) Meth. Enzymol. 187:167).

Synthesis of 15(±)methyl-cyclo-LXA₄

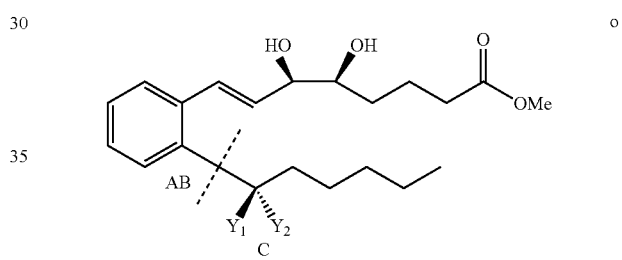

Compound o as the SiMe₃ derivative can be placed (~1 gm) in a round bottom 100 ml flask under an atmosphere enriched with argon in degassed benzene (20 ml). To this add 3.0 equivalents of a vinyl bromide fragment vide infra. This coupling reaction is carried out in catalytic amounts of Pd (PPh₃)₄ and CuI and can be monitored by injected aliquots of this suspension into RP-HPLC monitored by UV abundance with a rapid scanning diode. The progression line course 1-3 h at 23° C. after which the material is extracted with ethyl acetate: H₂O 4:1 v/v) and concentrated by rotoevaporation. The methyl ester can be saponified in LiOH/THF to give quantitative yields of the free carboxylic acid. Other derivatives can be prepared as above using fragment A with different fragment B moieties that have been substituted to give for example a dimethyl or other derivative. This can be obtained by taking the readily available ketone p and treating it with CH₃MgBr (60° C.) to generate q that can also be coupled to fragment A as above using conventional techniques such as Pd(O)-Cu (I) coupling. Increased chain length from C-15 can also be obtained.

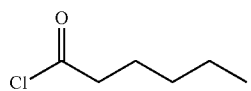

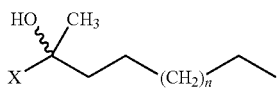

Synthesis of 5-Methyl-LXB$_4$ and 4,4-Dimethyl-LXB$_4$.

The 5-methyl-LXB$_4$ hinders or retards 5-oxo-LXB$_4$ formation. Using the general scheme outlined above, the A fragment can be constructed to carry the 5-methyl in a vinyl bromide r precursor that is coupled to a joined B+C fragment by Pd(0)-Cu(I) coupling.

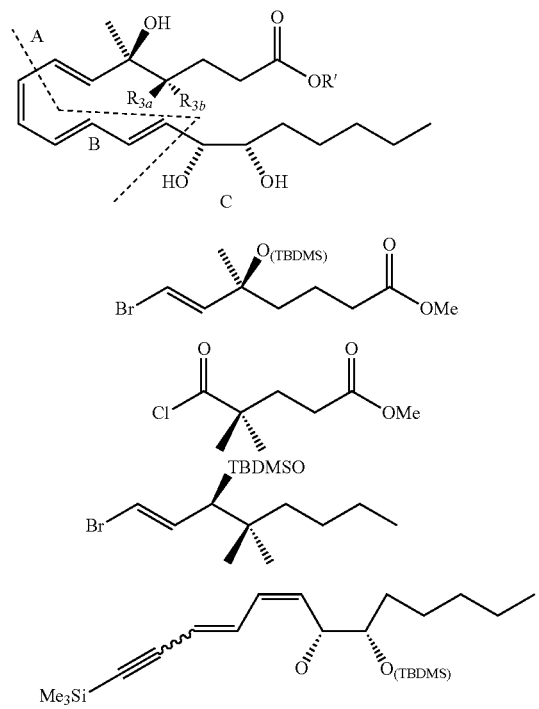

The vinyl bromide r can be obtained from the s that contains either dimethyl or hydrogen substituents at its C-4 position. The protected precursor t containing fragments B+C is generated as reported in reference (Nicolaou K. C. et al. (1991) Angew. Chem. Int. Ed. Engl. 30:1100-16.). Compound t is converted to s or 28 by coupling with the indicated vinyl bromide. Thus the target molecule can be generated by adding L at 1.0 equv. (≈1 gm) to a round bottom flask degassed containing Et$_2$NH as solvent with t injected in Et$_2$NH at 1.2 equiv. Pd(Ph$_3$P)$_4$ is added at 0.02 equiv. to give the 8(9)-containing acetylenic precursor methyl ester of s.

The material is extracted and subject to rotoevaporation suspended in quinoline (0.5 eq) in CH$_2$Cl$_2$ and subject to hydrogenation using (10%; 25° C.) Lindlar catalyst and a stream of H$_2$ gas to selectively reduce the acetylenic double bond at position 8. The formation of the tetraene component of the methylester of 5-methyl-LXB$_4$ or 4-dimethyl-LXB$_4$ methyl ester can be monitored by RP-HPLC to assess completion of the reduction (i.e., 1-3 h). The methyl#esters are next saponified to their corresponding free acids by treating the products with LiOH in THF 25 μH$_2$O added at 0=>241, 8-24 h.

EXAMPLE 4

Activity of Lipoxin Analogs on Columnar Epithelia

Several of the preferred lipoxin analogs (shown structurally as compounds 1 through 8 in Example 3) were prepared by total synthesis as described in Example 2. Following preparation and isolation of these compounds via HPLC, compounds were assessed to determine whether they retain biological activity using the epithelial cell transmigration assays as described above in Example 1.

Compounds 1 through 8 ($10^{-7}$-$10^{-10}$M) were found to inhibit neutrophil transmigration on epithelial cells. The acetylenic precursors (compound 1, 3, 5 and 7) were found to be physically more stable than their tetraene counterparts. Compound 7, which did not have an alcohol group in the C15 position or other modifications in the series, showed no biological activity in the assays. It would therefore appear that a substituent in the C15 position of lipoxin is necessary for the biological activity of at least lipoxin A$_4$ analogs. Lipoxin analogs 1 through 8 were found to block migration at potencies greater than or equal to synthetic lipoxin A$_4$. Compounds 1, 2 and 4 were found to be particularly effective. The results indicate that lipoxin A$_4$ analogs with modifications in C15-C20 positions retain their biological action and can inhibit PMN transmigration in columnar epithelia.

Equivalents

Those skilled in the art will recognize, or be able to ascertain using no more than routine experimentation, numerous equivalents to the specific procedures described herein. Such equivalents are considered to be within the scope of this invention and are covered by the following claims.

The invention claimed is:

1. A method for inhibiting inflammation in a subject caused or contributed to by PMN migration across columnar epithelia comprising, administering to a subject an effective amount of a lipoxin A$_4$ compound, selected from:

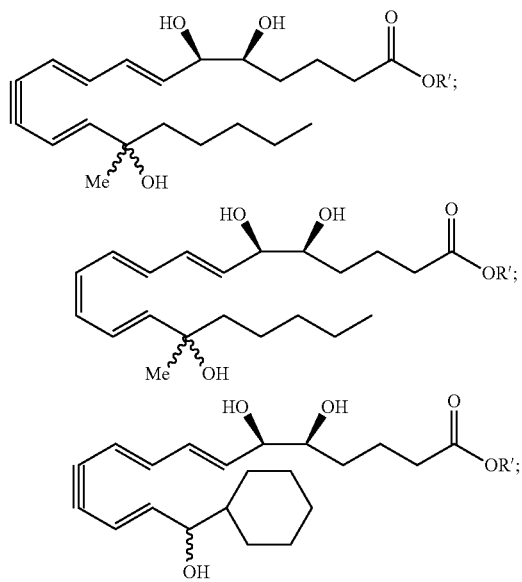

-continued
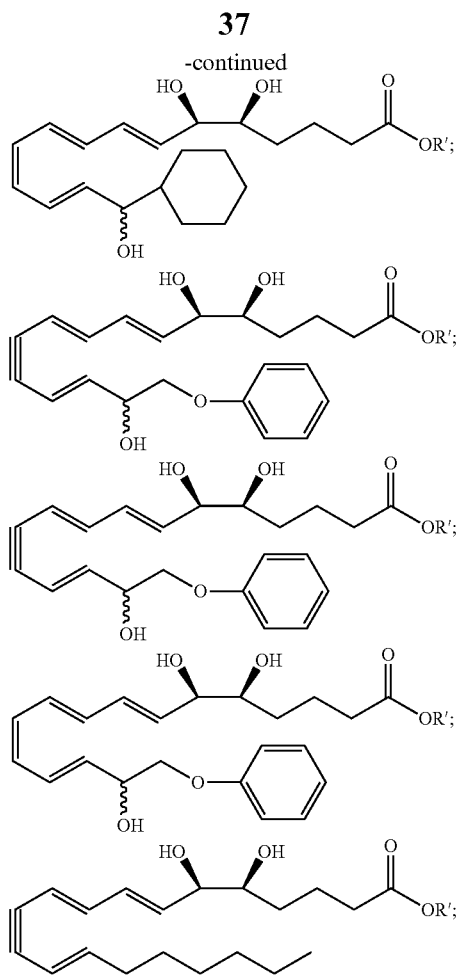
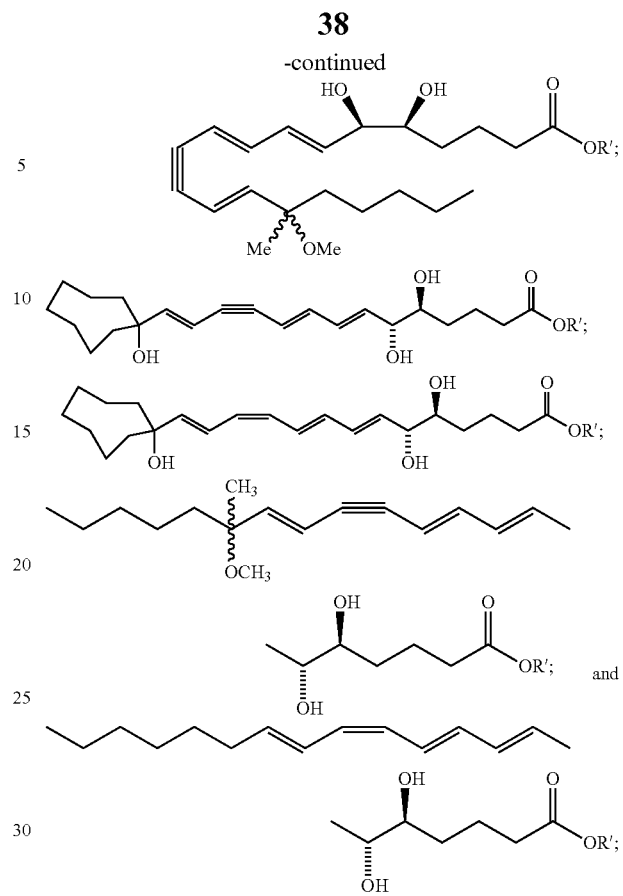
where R' is H or CH₃.
* * * * *